(12) United States Patent
Toledano et al.

(10) Patent No.: US 11,219,372 B2
(45) Date of Patent: Jan. 11, 2022

(54) DEVICE AND METHOD FOR CANCER DETECTION, DIAGNOSIS AND TREATMENT GUIDANCE USING ACTIVE THERMAL IMAGING

(71) Applicant: H.T BIOIMAGING LTD., Rishon le-Zion (IL)

(72) Inventors: Shani Toledano, Rishon le-Zion (IL); Yoav Rosenbach, Ramat Gan (IL); Moshe Tshuva, Tel Aviv (IL); Sharon Gat, Bat Hefer (IL)

(73) Assignee: H.T BIOIMAGING LTD., Rishon le-Zion (IL)

( * ) Notice: Subject to any disclaimer, the term of this patent is extended or adjusted under 35 U.S.C. 154(b) by 370 days.

(21) Appl. No.: 16/838,501

(22) Filed: Oct. 10, 2016

(65) Prior Publication Data
US 2020/0329975 A1 Oct. 22, 2020

Related U.S. Application Data

(63) Continuation-in-part of application No. PCT/IL2015/050392, filed on Apr. 13, 2015.
(Continued)

(51) Int. Cl.
*A61B 5/01* (2006.01)
*G16H 50/30* (2018.01)
(Continued)

(52) U.S. Cl.
CPC .............. *A61B 5/01* (2013.01); *A61B 5/0077* (2013.01); *A61B 5/015* (2013.01); *A61B 5/08* (2013.01);
(Continued)

(58) Field of Classification Search
CPC . G06T 2207/10048; G06T 2207/30096; G06T 2207/30104; G06T 7/0012;
(Continued)

(56) References Cited

U.S. PATENT DOCUMENTS

| 7,513,876 B2 | 4/2009 | Casscells et al. |
| 8,774,902 B2 | 7/2014 | Dekel et al. |

(Continued)

FOREIGN PATENT DOCUMENTS

| WO | 2008039388 A3 | 4/2008 |
| WO | 2015159284 A1 | 10/2015 |

OTHER PUBLICATIONS

Pirtini Cetingul et al, "Quantitative Evaluation of Skin Lesions Using Transient Thermal Imaging". Proceedings of the 2010 14th International Heat Transfer Conference. 2010 14th International Heat Transfer Conference, vol. 1. Washington, DC, USA. Aug. 8-13, 2010. pp. 31-39. ASME. https://doi.org/10.1115/IHTC14-22465.

*Primary Examiner* — Carolyn A Pehlke
(74) *Attorney, Agent, or Firm* — The Roy Gross Law Firm, LLC; Roy Gross

(57) ABSTRACT

The present invention discloses means and methods for detecting irregularities in the cells throughout a healthy tissue. The method generally relates to cancer detection, diagnosis and treatment, and more specifically pertains to detection, diagnosis and treatment guidance of cancerous or precancerous conditions through the use of thermal imaging technology and analysis.

17 Claims, 10 Drawing Sheets

Related U.S. Application Data

(60) Provisional application No. 62/110,615, filed on Feb. 2, 2015, provisional application No. 61/978,901, filed on Apr. 13, 2014.

(51) Int. Cl.
| | |
|---|---|
| *G16H 50/70* | (2018.01) |
| *G16H 50/20* | (2018.01) |
| *A61B 5/00* | (2006.01) |
| *G06T 7/00* | (2017.01) |
| *G01J 5/00* | (2006.01) |
| *A61B 5/08* | (2006.01) |
| *A61F 7/00* | (2006.01) |

(52) U.S. Cl.
CPC ............... *A61B 5/742* (2013.01); *A61F 7/00* (2013.01); *G06T 7/0012* (2013.01); *G16H 50/20* (2018.01); *G16H 50/30* (2018.01); *G16H 50/70* (2018.01); *A61B 2560/0252* (2013.01); *A61B 2562/0271* (2013.01); *G01J 5/00* (2013.01); *G01J 2005/0081* (2013.01); *G06T 2207/10048* (2013.01); *G06T 2207/30096* (2013.01); *G06T 2207/30104* (2013.01)

(58) Field of Classification Search
CPC ....... G01J 2005/0081; G01J 2005/0085; G01J 2005/0092; G01J 5/00; A61B 2562/0271; A61B 5/01; A61B 5/015; A61B 5/077; A61B 5/08; G16H 50/20; G16H 50/30; G16H 50/70
See application file for complete search history.

(56) References Cited

U.S. PATENT DOCUMENTS

| | | |
|---|---|---|
| 8,864,669 B2 | 10/2014 | Behar |
| 8,923,954 B2 | 12/2014 | Herman |
| 2004/0236225 A1 | 11/2004 | Murphy et al. |
| 2007/0106157 A1 | 5/2007 | Kaczkowski et al. |
| 2007/0213617 A1 | 9/2007 | Berman et al. |
| 2010/0222698 A1 | 9/2010 | Turnquist et al. |
| 2011/0021944 A1 | 1/2011 | Amon et al. |
| 2011/0066035 A1 | 3/2011 | Norris et al. |
| 2011/0087096 A1 | 4/2011 | Behar |
| 2011/0230942 A1 | 9/2011 | Herman et al. |
| 2012/0316439 A1 | 12/2012 | Behar |
| 2013/0116573 A1 | 5/2013 | Herman |
| 2018/0333105 A1* | 11/2018 | Hayat .................... G06T 7/277 |

* cited by examiner

| Plate marking and Cell Cataloging | | | | | | |
|---|---|---|---|---|---|---|
| Type | Kidney | Kidney Cancer | Lung | Lung Cancer | Lung | Lung Cancer |
| Catalog/source | AK-epithelial adult kidney | Wilm's tumor from exografts | Fibroblasts | H1299 | Fibroblasts | 549 |
| No. | 1 | 4 | 2 | 5 | 3 | 6 |

| Plate Layout | |
|---|---|
| 3. Lung Fibroblasts | 6. Lung Tumor – 549 |
| 2. Lung Fibroblasts | 5. Lung Tumor - H1299 |
| 1. Kidney - AK-epithelial | 4. Kidney - Wilm's tumor from exografts |

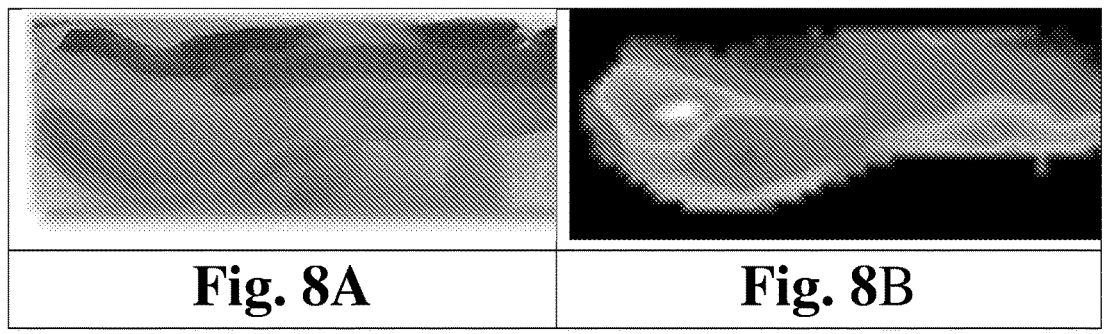
Fig. 8A | Fig. 8B
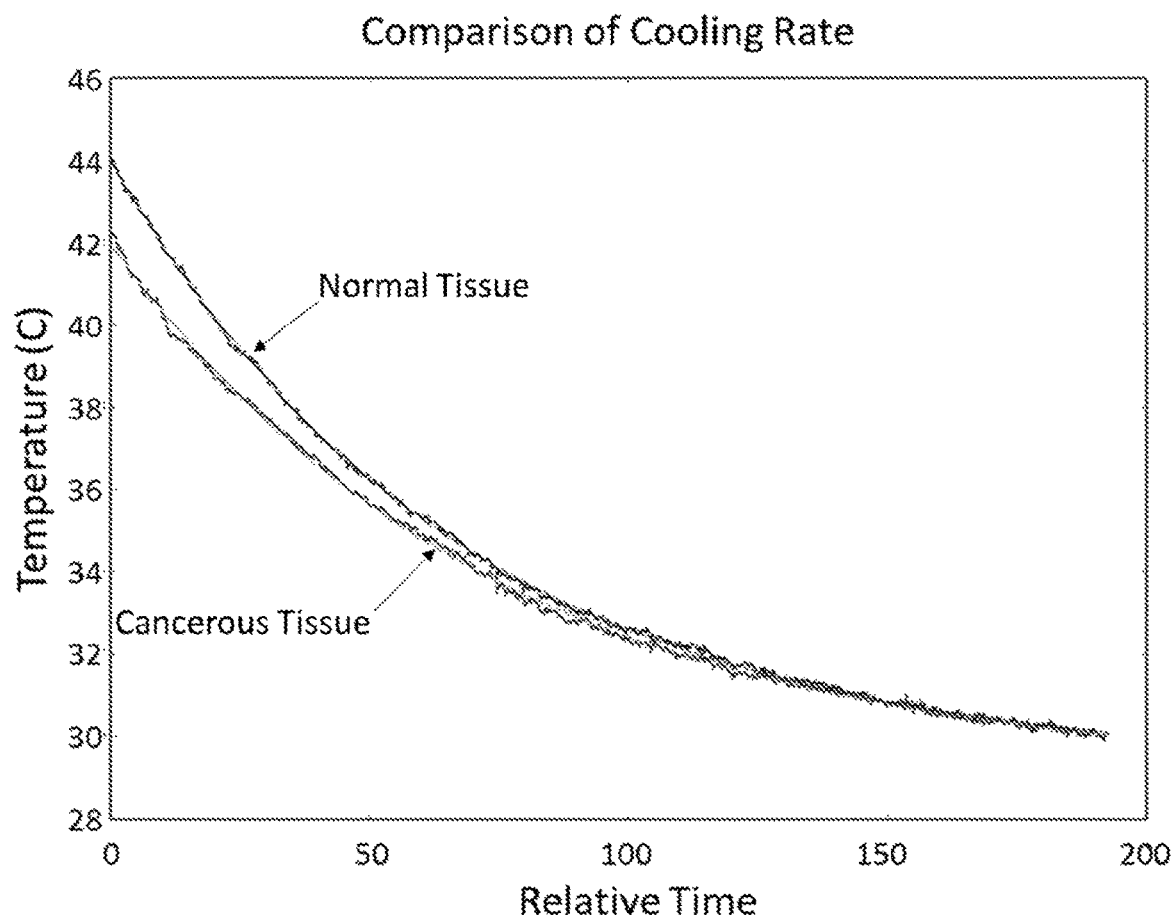
Fig. 9

DEVICE AND METHOD FOR CANCER DETECTION, DIAGNOSIS AND TREATMENT GUIDANCE USING ACTIVE THERMAL IMAGING

CROSS REFERENCE TO RELATED APPLICATIONS

This application is a Continuation-in-part of PCT Patent Application No. PCT/IL2015/050392 filed on Apr. 13, 2015, which claims the benefit of priority of U.S. Provisional Application No. 62/110,615 filed on Feb. 2, 2015 and U.S. Provisional Application No. 61/978,901 filed Apr. 13, 2014. The contents of the above applications are all incorporated by reference as if fully set forth herein in their entirety.

FIELD OF THE INVENTION

The present invention relates to cancer detection and diagnosis, and more specifically the present invention relates to cancer detection and diagnosis through the use of thermal imaging technology.

BACKGROUND OF THE INVENTION

Tumor cells are distinct from their surrounding normal tissue by several properties, one of which is a thermophysical property referred to as thermal diffusivity, which is expected to be different in cancerous cells compared to healthy cells. Thermal diffusivity is the combined property of density, heat capacity, thermal conductivity, blood perfusion and metabolic rate which are expected to be noticeably different in cancer cells. Importantly, even precancerous tissues or very young tumors appear to have distinct thermal diffusivity properties due to an enlarged nucleus, elevated crowdedness and more.

Lung cancer is considered the most deadly cancers in men and women worldwide. Lung cancer is the leading cause of cancer death among both men and women in the United States.

Statistical data regarding the extent of lung cancer states that lung cancer results in about 1.6 million deaths a year worldwide, being the leading cause of cancer death, at a total of 27% of all cancer related deaths. In the U.S. alone 228,190 new cases are diagnosed, and 160,000 deaths occur annually. In Israel 1,900 new cases are diagnosed and 1,600 deaths occur annually. Only 5% of lung cancers cases are diagnosed in stages that allow healing.

This extremely low survival rate of lung cancer is not due to lung tumors being more aggressive than other malignant tumors types, but in fact is due to the lack of early detection.

Since the lung contains no 'pain sensing' mechanism and its gas volume is much greater than its tissue volume, a tumor would hardly be noticed at early stages. Usually when the patient starts feeling any discomfort and turns to a physician, the tumor will already have exceeded the treatable size. Therefore breathing difficulties and coughing which usually leads to the diagnosis of the cancer means the tumor is large enough to be noticed and is probably untreatable. At this stage the cancer is progressive and usually metastatic and a targeted healing therapy cannot be considered, resulting in a five year survival rate which is very low.

In order to increase survival rate, many screening programs in the US use low dose CT. Screening reduced lung cancer deaths by 20%. But, while 25% of the tests are positive, 96% of all positive results are false and do not result in lung cancer diagnosis. About 30% of people with positive CT will go for a biopsy and only 20% of them will find out they have lung cancer.

These false positives lead to unnecessary biopsies and unnecessary treatment for healthy person. Therefore, a 'decision support' system, to inform a clinician whether the positive CT is a cancer and requires further investigation, would be of considerable utility. Such a system preferably provides immediate results, does not involve radiation risks and is independent of the need for an expert's eye. Preferably, such a test is computerized and automatic with no need for a long, expensive analysis stage.

In addition, oncologists treating the cancer have great difficulty in monitoring the treatment progress, and even cataloging the different stages of the disease. Many times, after a relatively long treating period, the physician would find the treatment had little to no effect. Treatment methods would then be changed, losing valuable time. In other cases cancer cells would successfully be destroyed, and turn into necrotic cells, however, traditional scans would not differentiate them from cancer cells. Usually in this case, an invasive lung biopsy is needed.

According to the World Health Organization (WHO), cervical cancer is the second most commonly prevalent cancer and the third greatest cause of death in women, with 530,000 new cases discovered each year.

Increasing incidences of weakened immune system, rapid spread of human papillomavirus (HPV) infection among the female population and long-term use of oral contraceptive pills are the primary factors responsible for the growth of cervical cancer.

Currently, cervical cancer screening includes a cytology-based screening, known as the Pap test or Pap smear. The main purpose of screening with the Pap test is to detect precancerous abnormal cells that may develop into cancer if left untreated, specifically Cervical Intraepithelial Neoplasia (CIN). In regularly screened populations, the Pap test identifies most abnormal cells before they become cancer. However, the Pap test should be taken with caution, as it is approximated that test incidence of false negatives can be as high as 20%-45%. Moreover, Pap test is expensive and requires 14-30 days of waiting for the cytology testing.

U.S. Pat. No. 8,774,902 discloses a device and method to diagnose an internal abnormality in a living subject by sensing a passively occurring electromagnetic radiation signal associated with the abnormality and inside an orifice of the subject, and U.S. Pat. No. 7,513,876 discloses a system for passively detecting thermal discrepancies in vessel walls. However, the use of passively occurring radiation only renders '902 to be incompetent in detecting minor differences in cell structure, which are already found in the precancerous stage.

U.S. Pat. No. 8,864,669 discloses a method for detecting abnormal tissue using ultrasound backscattered from the background. The detection is manifested through different tissues absorbing ultrasound differently.

U.S. Pat. No. 8,923,954 discloses an IR detection system for identifying malignant tumors by identifying areas of increased metabolic activity, and by assuming that malignant tumors have increased metabolic activity due to increased blood supply. However, patent '954 only identifies tumors which have grown in mass to such extent as to provide evidence of increased metabolic activity and blood supply.

US patent publication number US2013/0116573 and US Patent Publication number US2011/0230942 disclose a thermal imaging system to scan at least a section of a surface of a subject under observation, using both a geometrical scanning system and a thermal (IR) scanning system. A data processing system receives data from the geometrical scanning system, constructs a surface map of the section of the surface under observation and identifies geometrical markers on the surface map based on the data from the geometrical scanning system. The data processing system also receives data over a recovery time from the IR imaging system and constructs a thermal map of the section of the surface, identifying thermal markers on the thermal map based on the data from the infrared imaging system. The two maps are then registered based on a correspondence between at least some of the geometrical and thermal markers and the locations of lesions at the surface can be determined from the surface temperature profile as shown in the registered image. However, in the above documents, to Herman, the skin surface is cooled by application of cold fluid to a region of the surface, so that Herman can only identify lesions at or very near the surface.

Therefore, a long felt need still exists for a screening system and method which will provide early pre-cancerous diagnosis.

SUMMARY OF THE INVENTION

Therefore, detection of cancer cells using a thermal diffusivity imaging method is disclosed.

It is thus an object of the present invention to disclose a method for detecting and diagnosing of at least one irregularity in an examined tissue, characterized by steps of:
  actively thermomodulating at least a portion of said examined tissue, said active thermomodulation selected from a group consisting of heating, cooling and any combination thereof, said active thermomodulation applied according to a pre-determined protocol selected from a group consisting of: in a continuous manner, in a pulsed manner and any combination thereof;
  collecting time-resolved thermal data at predetermined time intervals over time t, of a plurality of coordinated locations of at least a portion of said examined tissue;
  calculating according to said time-resolved thermal data, a thermal transfer index, I, for each of said plurality of coordinated locations;
  wherein at least one of the following is being held true:
  if, for at least one of said plurality of coordinated locations, said I is greater than a predetermined value $I_{irr}$, determining tissue at said least one coordinated location as irregular;
  if, for at least one of said plurality of coordinated locations, a ratio between said I and a predetermined I-scale is greater than a predetermined value $I_{irr}$, determining tissue at said least one coordinated location as irregular;
  if, for at least two of said plurality of coordinated locations, a ratio between a first $I_{first}$ of a first coordinated location and a second $I_{second}$ of a second coordinated location is greater than a predetermined value $I_{irr}$, determining tissue at said first coordinated location as irregular
  further wherein said processor is configured to generate a three-dimensional visual presentation of said coordinated locations according to said I or an inferential thereof.

It is thus another object of the present invention to disclose the method as described above, further comprising a step of defining said I in a manner selected from:
  according to the following formula:
  $T = a + b * \exp(-I*t)$
  where T is temperature at said time t and a and b are constants;

according to the following formula:

$$\rho C \frac{\partial T}{\partial t} = \nabla(k \nabla T) + q + A_0 - b(T - T_b)$$

where:

$q \left[ \frac{W}{m^3} \right]$ is an external heat source;

$A_0 \left[ \frac{W}{m^3} \right]$ is a metabolic heat source;

$b \left[ \frac{W}{m^3 \, °C.} \right]$ is a heat loss due to blood perfusion; $T_b$ [° C.] is blood temperature;
  T [° C.] is temperature;

$\rho \left[ \frac{kg}{m^3} \right]$ is density;

$C_p \left[ \frac{J}{kg \, °C.} \right]$ is heat capacity; and $k \left[ \frac{W}{m \, °C.} \right]$ is thermal conductivity factor;
  from a thermal conductivity coefficient, from a thermal diffusion coefficient, from a heat capacity, from a density, from a heat loss due to blood perfusion, from a blood temperature, from a heat convection index, from a metabolic heat source and any combination thereof.

It is thus another object of the present invention to disclose the method as described above, further comprising at least one of the following steps:
  selecting said at least one irregularity from a group consisting of a malignant tumor, a precancerous tumor, a benign tumor, an infection, pneumonia, a necrotic cell, a blood clot and any combination thereof;
  selecting said examined tissue from a group consisting of lung tissue, skin, cervical tissue, ear tissue, nose tissue, throat tissue, oral tissue, esophageal tissue, stomach tissue, intestinal tissue, colon tissue, rectal tissue, kidney tissue, uterine tissue, urinary tract tissue, bladder tissue, prostate tissue, eye tissue, and any combination thereof; and selecting said time interval t to be in a range from about 10 ns to about 10 min.

It is thus another object of the present invention to disclose the method as described above, further comprising steps of collecting said thermal data using at least one sensor and of selecting said at least one sensor from a group consisting of: an IR sensor, a mercury-in-glass thermometer, pill thermometer, liquid crystal thermometer, thermocouple, thermistor, resistance temperature detector, silicon bandgap temperature sensor and any combination thereof.

It is thus another object of the present invention to disclose the method as described above, further comprising at least one of the following steps:

producing at least one heat diffusion image of at least a portion of said examined tissue prior to said active thermomodulation;

image processing said at least one heat diffusion image by at least one object recognition module, thereby identifying coordinated locations suspected of containing at least one said irregularity; and providing at least one spatial positioner selected from a group consisting of a visible light imaging means, a CCD camera, an ultrasound scanner, a thermal camera, a laser rangefinder and any combination thereof, and correlating said at least one heat diffusion image and at least one image from said at least one spatial positioner.

It is thus another object of the present invention to disclose the method as described above, further comprising a providing a normalization step, at least one of the following being held true:

said normalizing step comprises normalizing said I to a predetermined scale, a higher value on said scale indicating a higher severity of the medical condition of said at least one irregularity;

said normalizing step is selected from a group consisting of correcting to ambient temperature, correcting to ambient humidity, correcting to ambient electromagnetic radiation and any combination thereof;

said normalizing step is selected from a group consisting of correcting for ambient temperature, correcting for ambient humidity, correcting for ambient electromagnetic radiation and any combination thereof; and said heat transfer index is normalized with patient parameters selected from a group consisting of sex, age, smoking habits, drinking habits, number of births, height, weight, blood pressure, diabetes state, medical history, relatives medical history, patient's previous heat transfer index and any combination thereof.

It is thus another object of the present invention to disclose the method as described above, further comprising steps of selecting said active thermomodulation from a group consisting of advecting heat, convecting heat, conducting heat, irradiating and any combination thereof; and of selecting said active thermomodulation device from a group consisting of hot fluid inhalation, cold fluid inhalation, hot fluid application, cold fluid application, halogen lamp exposure, cold fluid xenon lamp exposure, flash lamp exposure, incandescent lamp exposure, IR emission, electromagnetic vibration heating, mechanical vibration heating, positioning a heatable solid, positioning a coolable solid, positioning a heatable patch, positioning a coolable patch, pharmaceutical temperature modification, chemically induced heating, chemically induced cooling and any combination thereof.

It is thus another object of the present invention to disclose a system for detecting and diagnosing at least one irregularity in an examined tissue, comprising:

an active thermomodulator configured to apply to at least a portion of said examined tissue a member of a group consisting of: heating cooling and any combination thereof, said active thermomodulation applicable according to a pre-determined protocol selected from a group consisting of: in a continuous manner, in a pulsed manner and any combination thereof;

at least one thermal sensor configured to provide at least one signal related to temperature in at least a part of said at least a portion of said examined tissue; and a processor configured to execute instructions comprising:

collect time-resolved thermal data, at predetermined intervals over time t, of a plurality of coordinated locations of at least a portion of said examined tissue by conversion of said signal from said at least one thermal sensor to time-resolved and spatially-resolved thermal data; and calculate, according to said time-resolved thermal data, a thermal transfer index, I, for each of said plurality of coordinated locations;

wherein at least one of the following is being held true:

if, for at least one of said plurality of coordinated locations, said I is greater than a predetermined value $I_{irr}$, tissue at said least one coordinated location is determinable as irregular;

if, for at least one of said plurality of coordinated locations, a ratio between said I and a predetermined I-scale is greater than a predetermined value $I_{irr}$, tissue at said least one coordinated location is determinable as irregular;

if, for at least two of said plurality of coordinated locations, a ratio between a first $I_{first}$ of a first coordinated location and a second $I_{second}$ of a second coordinated location is greater than a predetermined value $I_{irr}$, tissue at said first coordinated location is determinable as irregular;

further wherein said processor is configured to generate at least one of a group consisting of a two-dimensional thermal map or a three-dimensional thermal diffusion image of said at least a portion of said examined tissue.

It is thus another object of the present invention to disclose the system as described above, wherein said I is definable in a manner selected from:

according to the following formula:

$$T = a + b^* \exp(-I^* t)$$

where T is temperature at said time t and a and b are constants;

according to the following formula:

$$\rho C \frac{\partial T}{\partial t} = \nabla (k \nabla T) + q + A_0 - b(T - T_b)$$

where:

$$q \left[ \frac{W}{m^3} \right]$$

is an external heat source;

$$A_0 \left[ \frac{W}{m^3} \right]$$

is a metabolic heat source;

$$b \left[ \frac{W}{m^3 \, °C.} \right]$$

is a heat loss due to blood perfusion; $T_b$ [° C.] is blood temperature;
T [° C.] is temperature;

$$\rho \left[ \frac{kg}{m^3} \right]$$

is density;

$$C_p \left[ \frac{J}{kg \, °C.} \right]$$

is heat capacity; and $$k \left[ \frac{W}{m \, °C.} \right]$$

is thermal conductivity factor;
from a thermal conductivity coefficient, from a thermal diffusion coefficient, from a heat capacity, from a density, from a heat loss due to blood perfusion, from a blood temperature, from a heat convection index, from a metabolic heat source and any combination thereof.

It is thus another object of the present invention to disclose the system as described above, wherein at least one of the following is held true:
said at least one irregularity is selected from a group consisting of a malignant tumor, a precancerous tumor, a benign tumor, an infection, pneumonia, a necrotic cell, a blood clot and any combination thereof;
said examined tissue is selected from a group consisting of lung tissue, skin, cervical tissue, ear tissue, nose tissue, throat tissue, oral tissue, esophageal tissue, stomach tissue, intestinal tissue, colon tissue, rectal tissue, kidney tissue, uterine tissue, urinary tract tissue, bladder tissue, prostate tissue, eye tissue, and any combination thereof; and
said time t is selected to be in a range from about 10 ns to about 10 min.

It is thus another object of the present invention to disclose the system as described above, wherein said at least one sensor is selected from a group consisting of: an IR sensor, a mercury-in-glass thermometer, pill thermometer, liquid crystal thermometer, thermocouple, thermistor, resistance temperature detector, silicon bandgap temperature sensor and any combination thereof.

It is thus another object of the present invention to disclose the system as described above, wherein at least one of the following is held true:

at least one heat diffusion image of at least a portion of said examined tissue is producible prior to said active thermomodulation;
at least one coordinated location suspected of containing at least one irregularity is identifiable by means of image processing of said at least one heat diffusion image by at least one object recognition module; and
said system additionally comprises at least one spatial positioner selected from a group consisting of: a visible light imaging means, a CCD camera, an ultrasound scanner, a thermal camera, a laser rangefinder and any combination thereof, and said processor additionally comprises instructions configured to correlate said at least one heat diffusion image and at least one image from said at least one spatial positioner.

It is thus another object of the present invention to disclose the system as described above, wherein said computer program additionally comprises instructions to provide a normalization step, at least one of the following being held true:
said normalizing step comprises normalizing said I to a predetermined scale, a higher value on said scale indicating a higher severity of the medical condition of said at least one irregularity;
said normalizing step is selected from a group consisting of correcting to ambient temperature, correcting to ambient humidity, correcting to ambient electromagnetic radiation and any combination thereof;
said normalizing step is selected from a group consisting of correcting for ambient temperature, correcting for ambient humidity, correcting for ambient electromagnetic radiation and any combination thereof; and
said heat transfer index is normalized with patient parameters selected from a group consisting of sex, age, smoking habits, drinking habits, number of births, height, weight, blood pressure, diabetes state, medical history, relatives medical history, patient's previous heat transfer index and any combination thereof.

It is thus another object of the present invention to disclose the system as described above, wherein said active thermomodulation is selected from a group consisting of advecting heat, convecting heat, conducting heat, irradiating and any combination thereof; and said active thermomodulation device is selected from a group consisting of hot fluid inhalation, cold fluid inhalation, hot fluid application, halogen lamp exposure, LED light exposure, xenon lamp exposure, flash lamp exposure, incandescent lamp exposure, IR emission, electromagnetic vibration heating, mechanical vibration heating, positioning a heatable solid, positioning a coolable solid, positioning a heatable patch, positioning a coolable patch, pharmaceutical temperature modification, chemically induced heating, chemically induced cooling and any combination thereof.

It is thus another object of the present invention to disclose a computer readable medium (CRM) having instructions which, when implemented by one or more computers, causes said one or more computers to:
collect time-resolved thermal data, at predetermined intervals over time t, of a plurality of coordinated locations of at least a portion of said examined tissue by conversion of said signal from said at least one thermal sensor to time-resolved and spatially-resolved thermal data; and
calculate, according to said time-resolved thermal data, a thermal transfer index, I, for each of said plurality of coordinated locations;

wherein at least one of the following is being held true:
if, for at least one of said plurality of coordinated locations, said I is greater than a predetermined value $I_{irr}$, determine tissue at said least one coordinated location as irregular;
if, for at least one of said plurality of coordinated locations, a ratio between said I and a predetermined I-scale is greater than a predetermined value $I_{irr}$, determine tissue at said least one coordinated location as irregular;
if, for at least two of said plurality of coordinated locations, a ratio between a first $I_{first}$ of a first coordinated location and a second $I_{second}$ of a second coordinated location is greater than a predetermined value $I_{irr}$, determine tissue at said first coordinated location as irregular;
further wherein said CRM comprises instructions configured to generate a three or two-dimensional thermal diffusion image of said at least a portion of said examined tissue.

It is thus another object of the present invention to disclose the CRM as described above, additionally comprising instructions configured to calculate said I in a manner selected from:
according to the following formula:
$$T=a+b*\exp(-I*t)$$
where T is temperature at said time t and a and b are constants;
according to the following formula:
$$\rho C \frac{\partial T}{\partial t} = \nabla(k\nabla T) + q + A_0 - b(T - T_b)$$
where:
$$q\left[\frac{W}{m^3}\right]$$
is an external heat source;
$$A_0\left[\frac{W}{m^3}\right]$$
is a metabolic heat source;
$$b\left[\frac{W}{m^3 °C.}\right]$$
is a heat loss due to blood perfusion; $T_b$ [° C.] is blood temperature;
T [° C.] is temperature;
$$\rho\left[\frac{kg}{m^3}\right]$$
is density;
$$C_p\left[\frac{J}{kg °C.}\right]$$
is heat capacity; and
$$k\left[\frac{W}{m °C.}\right]$$
is thermal conductivity factor;
from a thermal conductivity coefficient, from a thermal diffusion coefficient, from a heat capacity, from a density, from a heat loss due to blood perfusion, from a blood temperature, from a heat convection index, from a metabolic heat source and any combination thereof.

It is thus another object of the present invention to disclose the CRM as described above, wherein at least one of the following is held true:
said at least one irregularity is selected from a group consisting of a malignant tumor, a precancerous tumor, a benign tumor, an infection, pneumonia, a necrotic cell, a blood clot and any combination thereof;
said examined tissue is selected from a group consisting of lung tissue, skin, cervical tissue, ear tissue, nose tissue, throat tissue, oral tissue, esophageal tissue, stomach tissue, intestinal tissue, colon tissue, rectal tissue, kidney tissue, uterine tissue, urinary tract tissue, bladder tissue, prostate tissue, eye tissue, and any combination thereof; and
said time t is selected to be in a range from about 10 ns to about 10 min.

It is thus another object of the present invention to disclose the CRM as described above, additionally comprising instructions configured to execute at least one of the following:
produce at least one heat diffusion image of at least a portion of said examined tissue prior to said active thermomodulation;
identify at least one coordinated location suspected of containing at least one irregularity by means of image processing of said at least one heat diffusion image by at least one object recognition module; and
correlate said at least one heat diffusion image and at least one image from at least one spatial positioner, said at least one spatial positioner selected from a group consisting of: a visible light imaging means, a CCD camera, an ultrasound scanner, a thermal camera, a laser rangefinder and any combination thereof.

It is thus another object of the present invention to disclose the CRM as described above, additionally comprising instructions configured to provide a normalization step, at least one of the following being held true:
said normalizing step comprises normalizing said I to a predetermined scale, a higher value on said scale indicating a higher severity of the medical condition associated with said at least one irregularity;
said normalizing step is selected from a group consisting of correcting to ambient temperature, correcting to ambient humidity, correcting to ambient electromagnetic radiation and any combination thereof;
said normalizing step is selected from a group consisting of correcting for ambient temperature, correcting for ambient humidity, correcting for ambient electromagnetic radiation and any combination thereof; and
said heat transfer index is normalized with patient parameters selected from a group consisting of sex, age, smoking habits, drinking habits, number of births, height, weight, blood pressure, diabetes state, medical history, relatives medical history, patient's previous heat transfer index and any combination thereof.

It is thus another object of the present invention to disclose the CRM as described above, wherein said active thermomodulation is selected from a group consisting of advecting heat, convecting heat, conducting heat, irradiating and any combination thereof; and said active thermomodulation device is selected from a group consisting of hot fluid inhalation, cold fluid inhalation, hot fluid application, cold fluid application, halogen lamp exposure, LED light exposure, xenon lamp exposure, flash lamp exposure, incandescent lamp exposure, IR emission, electromagnetic vibration heating, mechanical vibration heating, positioning a heatable solid, positioning a coolable solid, positioning a heatable patch, positioning a coolable patch, pharmaceutical temperature modification, chemically induced heating, chemically induced cooling and any combination thereof.

It is thus another object of the present invention to disclose a method for detecting and diagnosing at least one irregularity in the tissue's cells in an examined tissue, characterized by steps of: actively thermomodulating said examined tissue, or a portion thereof; collecting time-resolved thermal data, over time t, of a plurality of coordinated locations of said examined tissue; calculating according to said time-resolved thermal data, a thermal transfer index, I, for each of said plurality of coordinated locations; wherein at least one of the following is being held true: if said I is greater than a predetermined value $I_{irr}$, determining said tissue as irregular; if a ratio between said I and a predetermined I-scale is greater than a predetermined value $I_{irr}$, determining said tissue as irregular; if a ratio between a first $I_{first}$ of a first coordinated location and a second $I_{second}$ of a second coordinated location is greater than a predetermined value $I_{irr}$, determining said tissue as irregular.

It is another object of the present invention to disclose a method for detecting and diagnosing at least one irregularity in the tissue's cells in an examined tissue, characterized by steps of: actively thermomodulating said examined tissue, or a portion thereof; collecting time-resolved thermal data, over time t, of at least one coordinated location of said examined tissue; calculating according to said time-resolved thermal data, a thermal transfer index, I, for each of said coordinated locations; wherein said I is defined according to the following formula: $T=a+b*\exp(-I*t)$ where a and b are constants and T is temperature.

It is also an object of the present invention to provide the abovementioned method, wherein if said I is greater than a predetermined value $I_{irr}$, determining said tissue as irregular.

It is also an object of the present invention to provide the abovementioned method, wherein if a ratio between said I and a predetermined I-scale is greater than a predetermined value $I_{irr}$, determining said tissue as irregular.

It is also an object of the present invention to provide the abovementioned method, wherein if a ratio between a first $I_{first}$ of a first coordinated locations and a second $I_{second}$ of a second coordinated locations is greater than a predetermined value $I_{irr}$, determining said tissue as irregular.

It is also an object of the present invention to provide any of the abovementioned methods, further comprising steps of constructing a visual presentation of said coordinated locations according to said I or an inferential thereof.

It is also an object of the present invention to provide any of the abovementioned methods, wherein said I is selected from the group consisting of an exponential decay constant calculated according to said time-resolved thermal data, thermal conductivity coefficient, thermal diffusion coefficient, heat capacity, density, heat loss due to blood perfusion, blood temperature, heat convection index, metabolic heat source and any combination thereof.

It is also an object of the present invention to provide any of the abovementioned methods, further comprising steps of image processing said visual presentation by an object recognition module, thereby identifying coordinated locations suspected of containing at least one irregularity in the tissue's cells.

It is also an object of the present invention to provide any of the abovementioned methods, further comprising the step of normalizing said I to a predetermined scale.

It is also an object of the present invention to provide any of the abovementioned methods, wherein said time-resolved thermal data is a temperature measurement taken at predetermined intervals over time.

It is also an object of the present invention to provide any of the abovementioned methods, further comprising normalization steps selected from the group consisting of normalizing said I to ambient temperature, correcting to ambient humidity, correcting to ambient electromagnetic radiation and any combination thereof.

It is also an object of the present invention to disclose any of the aforementioned systems, further comprising a spatial positioning means selected from the group consisting of a visible light imaging means, a CCD camera, an ultrasound scanner, a thermal camera, a laser rangefinder and any combination thereof.

It is also an object of the present invention to provide a non-transitory computer readable medium (CRM) having instructions which, when implemented by one or more computers cause said one or more computers to: store time-resolved thermal data of a plurality of coordinated locations of an examined tissue, or portion thereof, collected over time t; calculate according to said time-resolved thermal data, a thermal transfer index, I, for each of said plurality of coordinated locations; wherein at least one of the following is being held true: if said I is greater than a predetermined value $I_{irr}$, determining said tissue as irregular; if a ratio between said I and a predetermined I-scale is greater than a predetermined value $I_{irr}$, determining said tissue as irregular; if a ratio between a first $I_{first}$ of a first coordinated location and a second $I_{second}$ of a second coordinated location is greater than a predetermined value $I_{irr}$, determining said tissue as irregular.

It is yet another object of the present invention to provide a non-transitory computer readable medium (CRM) having instructions which, when implemented by one or more computers cause said one or more computers to: store time-resolved thermal data of a plurality of coordinated locations of an examined tissue, or portion thereof, collected over time t; calculate according to said time-resolved thermal data, a thermal transfer index, I, for each of said plurality of coordinated locations; wherein said I is defined according to the following formula: $T=a+b*\exp(-I*t)$ where a and b are constants and T is temperature.

It is thus one object of the present invention to disclose a method for detecting and diagnosing at least one irregularity in the tissue's cells in an examined tissue, characterized by steps of: actively thermomodulating said examined tissue, or a portion thereof; collecting time-resolved thermal data, over time t, of a plurality of coordinated locations of said examined tissue; calculating according to said time-resolved thermal data, a thermal transfer index, I, for each of said plurality of coordinated locations; wherein at least one of the following is being held true: if said I is greater than a predetermined value $I_{irr}$, determining said tissue as irregular; if a ratio between said I and a predetermined I-scale is greater than a predetermined value $I_{irr}$, determining said tissue as irregular; if a ratio between a first $I_{first}$ of a first coordinated location and a second $I_{second}$ of a second coordinated location is greater than a predetermined value $I_{irr}$, determining said tissue as irregular.

It is another object of the present invention to disclose method for detecting and diagnosing at least one irregularity in the tissue's cells in an examined tissue, characterized by steps of: actively thermomodulating said examined tissue, or a portion thereof; collecting time-resolved thermal data, over time t, of at least one coordinated location of said examined tissue; calculating according to said time-resolved thermal data, a thermal transfer index, I, for each of said coordinated locations; wherein said I is defined according to the following formula: $T=a+b*\exp(-I*t)$ where T is the temperature and a and b are constants.

It is also an object of the present invention to provide the abovementioned method, wherein if said I is greater than a predetermined value $I_{irr}$, determining said tissue as irregular.

It is also an object of the present invention to provide the abovementioned method, wherein if a ratio between said I and a predetermined I-scale is greater than a predetermined value $I_{irr}$, determining said tissue as irregular.

It is also an object of the present invention to provide the abovementioned method, wherein if a ratio between a first $I_{first}$ of a first coordinated locations and a second $I_{second}$ of a second coordinated locations is greater than a predetermined value $I_{irr}$, determining said tissue as irregular.

It is also an object of the present invention to provide any of the abovementioned methods, further comprising steps of constructing a visual presentation of said coordinated locations according to said I or an inferential thereof.

It is also an object of the present invention to provide any of the abovementioned methods, wherein said I is selected from the group consisting of an exponential decay constant calculated according to said time-resolved thermal data, thermal conductivity coefficient, thermal diffusion coefficient, heat capacity, density, heat loss due to blood perfusion, blood temperature, heat convection index, metabolic heat source and any combination thereof.

It is also an object of the present invention to provide any of the abovementioned methods, further comprising steps of image processing said visual presentation by an object recognition module, thereby identifying coordinated locations suspected of containing at least one irregularity in the tissue's cells.

It is also an object of the present invention to provide any of the abovementioned methods, further comprising the step of normalizing said I to a predetermined scale.

It is also an object of the present invention to provide any of the abovementioned methods, wherein said time-resolved thermal data is a temperature measurement taken at predetermined intervals over time.

It is also an object of the present invention to provide any of the abovementioned methods, further comprising normalization steps selected from the group consisting of normalizing said I to ambient temperature, correcting to ambient humidity, correcting to ambient electromagnetic radiation and any combination thereof.

It is also an object of the present invention to disclose any of the aforementioned systems, further comprising a spatial positioning means selected from the group consisting of a visible light imaging means, a CCD camera, an ultrasound scanner, a thermal camera, a laser rangefinder and any combination thereof.

It is also an object of the present invention to provide a non-transitory computer readable medium (CRM) having instructions which, when implemented by one or more computers cause said one or more computers to: store time-resolved thermal data of a plurality of coordinated locations of an examined tissue, or portion thereof, collected over time t; calculate according to said time-resolved thermal data, a thermal transfer index, I, for each of said plurality of coordinated locations; wherein at least one of the following is being held true: if said I is greater than a predetermined value $I_{irr}$, determining said tissue as irregular; if a ratio between said I and a predetermined I-scale is greater than a predetermined value $I_{irr}$, determining said tissue as irregular; if a ratio between a first $I_{first}$ of a first coordinated location and a second $I_{second}$ of a second coordinated location is greater than a predetermined value $I_{irr}$, determining said tissue as irregular.

It is yet another object of the present invention to provide a non-transitory computer readable medium (CRM) having instructions which, when implemented by one or more computers cause said one or more computers to: store time-resolved thermal data of a plurality of coordinated locations of an examined tissue, or portion thereof, collected over time t; calculate according to said time-resolved thermal data, a thermal transfer index, I, for each of said plurality of coordinated locations; wherein said I is defined according to the following formula: $T=a+b*\exp(-I*t)$ where T is the temperature and a and b are constants.

It is another object of the present invention to provide a method for detecting and diagnosing at least one irregularity in the tissue's cells in an examined tissue, characterized by the steps of: applying thermomodulating means to at least a portion of the examined tissue; collecting at least one thermal data of at least a portion of the tissue over time; and calculating at least one heat transfer index of the thermal data over time; thereby detecting and diagnosing at least one irregularity in the tissue's cells according to the at least one heat transfer index; wherein the heat transfer index is calculated according to a derivative of the thermal data over time.

It is another object of the present invention to provide the above mentioned method, further comprising the step of selecting the derivative to be from the group consisting of first derivative, second derivative, third derivative and any combination thereof.

It is another object of the present invention to provide the above mentioned method, further comprising the step of normalizing the heat transfer index to a predetermined scale.

It is another object of the present invention to provide the above mentioned method, wherein the scale is a numerical scale between 1 and 10, further wherein a higher value indicates a higher severity of the medical condition of the at least one irregularity in the tissue's cells.

It is another object of the present invention to provide the above mentioned method, further comprising the step of correlating the heat transfer index with associated at least one irregularity in the tissue's cells selected from the group consisting of malignant tumors, precancerous tumors, benign tumors, infections, pneumonia, necrotic cells and any combination thereof.

It is another object of the present invention to provide the above mentioned method, further comprising the step of collecting the thermal data using a sensor selected from the group consisting of an IR sensor, a mercury-in-glass thermometer, pill thermometer, liquid crystal thermometer, thermocouple, thermistor, resistance temperature detector, silicon bandgap temperature sensor and any combination thereof.

It is another object of the present invention to provide the above mentioned method, wherein the at least one thermal data is a temperature measurement of the at least a portion of the tissue over time.

It is another object of the present invention to provide the above mentioned method, further comprising the steps of: collecting thermal image data of at least a portion of the tissue over time; calculating heat transfer index of the thermal image data over time; constructing a heat transfer map comprising, optionally spatial (i.e. three-dimensional), locations of the heat transfer index over time; and identifying a designated location in the heat diffusion image having distinctive heat transfer index from surrounding spatial locations.

It is another object of the present invention to provide the above mentioned method, further comprising the step of producing a heat diffusion image of the at least a portion of the tissue prior to the applying thermomodulating means to the tissue.

It is another object of the present invention to provide the above mentioned method, further comprising the step of deeming a designated spatial location of the heat transfer map suspect of at least one irregularity in the tissue's cells if the designated spatial location has the heat transfer index falling within a predetermined heat transfer index range.

It is another object of the present invention to provide the above mentioned method, wherein the spatial location is selected from the group consisting of one pixel, a plurality of pixels, a sub-pixel and any combination thereof.

It is another object of the present invention to provide the above mentioned method, further comprising the step of comparing the heat transfer map to a spatial image of the examined tissue's area.

It is another object of the present invention to provide the above mentioned method, further comprising a step of selecting said time t to be in a range from about 10 ns to about 10 min.

It is another object of the present invention to provide the above mentioned method, wherein during the step of applying thermomodulating means to the tissue, the method further comprises the steps of: collecting thermal data of at least a portion of the tissue over time, for tracking the thermoregulation; and calculating heat transfer index of the thermal data in real-time.

It is another object of the present invention to provide the above mentioned method, further comprising the step of constructing a heat transfer map comprising spatial locations of the real-time heat transfer index.

It is another object of the present invention to provide the above mentioned method, further comprising normalization steps selected from the group consisting of correcting to ambient temperature, correcting to ambient humidity, correcting to ambient electromagnetic radiation and any combination thereof.

It is another object of the present invention to provide the above mentioned method, further comprising the steps of providing access to a cervix area by a mechanical speculum; applying the heating and/or cooling to the cervix area; and correlating the heat transfer index with Cervical Intraepithelial Neoplasia (CIN).

It is another object of the present invention to provide the above mentioned method, further comprising the step of deriving the examined tissue from a mammal selected from the group consisting of human, monkey, rodent, sheep, goat, cow, horse and swine.

It is another object of the present invention to provide the above mentioned method, wherein the examined tissue is selected from the group consisting of lungs, skin, cervix, ear, nose, throat, oral cavities, esophagus, stomach, intestine, colon, rectum, kidney, uterus, urinary tract, bladder, prostate, eyes, and any part of the human body.

It is another object of the present invention to provide the above mentioned method, further comprising the step of selecting the thermomodulating means to operate in a manner selected from the group consisting of advection, convection, conduction, radiation and any combination thereof.

It is another object of the present invention to provide the above mentioned method, wherein the thermomodulating means is selected from the group consisting of heating means, cooling means and any combination thereof.

It is another object of the present invention to provide the above mentioned method, further comprising the step of applying the heating and/or cooling means by a method selected from the group consisting of hot and/or cold fluid inhalation, hot and/or cold fluid application, halogen lamp exposure, LED light exposure, xenon lamp exposure, flash lamp exposure, incandescent lamp exposure, IR emission, radiation, electromagnetic and/or mechanical vibration heating, hot and/or cold solid positioning, hot and/or cold patch positioning, pharmaceutical heat modification, chemically induced heating and/or cooling and any combination thereof.

It is another object of the present invention to provide the above mentioned method, wherein the step of collecting thermal data of at least a portion of the tissue over time is conducted by a thermal sensor positioned in a position selected from the group consisting of mounted outside the body, inserted to the body in an invasive procedure, inserted to the body in a semi-invasive procedure and any combination thereof.

It is another object of the present invention to provide the above mentioned method, further comprising the step of calculating the heat transfer index according to the thermal sensor resolution and sampling rate.

It is another object of the present invention to provide the above mentioned method, wherein the examined tissue is a biopsy sampling of a suspected tissue area.

It is another object of the present invention to provide the above mentioned method, further comprising the steps of applying the method to a second examined tissue being a biopsy sampling of a healthy tissue area, and obtained heat transfer index is compared between the suspected tissue area and the healthy tissue area.

It is another object of the present invention to provide the above mentioned method, further comprising the steps of using the heat transfer index for at least one of the following: detecting and mapping tumor boundaries for tumor removal operations; and determining medical severity and/or malignancy status of the at least one irregularity in the tissue's cells.

It is another object of the present invention to provide the above mentioned method, further comprising the step of normalizing the heat transfer index with patient parameters selected from the group consisting of sex, age, smoking habits, drinking habits, number of births, height, weight, blood pressure, diabetes state, medical history, relatives medical history, patient's previous heat transfer index and any combination thereof.

It is another object of the present invention to provide the above mentioned method, further comprising the steps of: applying thermomodulating means to a second tissue; collecting second thermal data of at least a portion of the second tissue over time; calculating a baseline heat transfer index of the second heat diffusion image data over time; comparing the baseline heat transfer index to the heat transfer index of the examined tissue; and detecting and diagnosing at least one irregularity in the tissue's cells according to a difference between the baseline heat transfer index of the second tissue to the heat transfer index of the examined tissue.

It is another object of the present invention to provide the above mentioned method, wherein at least one of the following is being held true: the second tissue is healthy; the second tissue comprises at least one irregularity in the tissue's cells;

It is another object of the present invention to provide the above mentioned method, further comprising the step of obtaining the baseline heat transfer index from a database comprising heat transfer index obtained from at least one second tissue deriving from an examined individual and/or from at least one second examined individuals.

It is another object of the present invention to provide the above mentioned method, further comprising the step of deriving a ratio between the heat transfer index of the examined tissue and a second heat transfer index of a second examined tissue, and comparing the ratio to at least one second ratio between a third heat transfer index of a third examined tissue, and a fourth heat transfer index of a fourth examined tissue.

It is another object of the present invention to provide the above mentioned method, wherein the second examined tissue is tissue surrounding the first tissue.

It is another object of the present invention to provide the above mentioned method, further comprising the step of obtaining the third distinctive heat transfer index and fourth heat transfer index from a database comprising heat transfer index obtained from a plurality of tissues deriving from an examined individual and/or a plurality of examined individuals.

It is another object of the present invention to provide the above mentioned method, further comprising the step of storing the baseline heat transfer index in a storing means selected from the group consisting of a computer readable medium, a server, a cloud-like server and any combination thereof.

It is another object of the present invention to provide the above mentioned method, further comprising the steps of applying the thermomodulating means according to a manner selected from the group consisting of according to a pre-determined protocol, in a continuous manner, in a pulse manner and any combination thereof.

It is also an object of the present invention to disclose a system for detecting and diagnosing at least one irregularity in the tissue's cells in an examined tissue, comprising: a thermomodulating means for applying heating and/or cooling to at least a portion of the examined tissue; a thermal sensor for collecting at least one thermal data of at least a portion of the examined tissue over time; and a processor adapted to read a computer readable medium with instructions for calculating at least one heat transfer index of the thermal data over time; thereby detecting and diagnosing at least one irregularity in the tissue's cells according to the at least one heat transfer index; wherein the heat transfer index is calculated according to a derivative of the thermal data over time.

It is still an object of the present invention to disclose the aforementioned system, wherein the derivative is selected from the group consisting of first derivative, second derivative, third derivative and any combination thereof.

It is still an object of the present invention to disclose the aforementioned system, wherein the processor is further adapted to normalize the heat transfer index to a predetermined scale.

It is still an object of the present invention to disclose the aforementioned system, wherein the scale is a numerical scale between 1 and 10, further wherein a higher value indicates a higher severity of the medical condition of the at least one irregularity in the tissue's cells.

It is still an object of the present invention to disclose the aforementioned system, wherein the processor is further adapted to read a computer readable medium with instructions for correlating the heat transfer index with associated at least one irregularity in the tissue's cells selected from the group consisting of malignant tumors, precancerous tumors, benign tumors, infections, pneumonia, necrotic cells and any combination thereof.

It is still an object of the present invention to disclose the aforementioned system, wherein the thermal sensor is selected from the group consisting of an IR sensor, a mercury-in-glass thermometer, pill thermometer, liquid crystal thermometer, thermocouple, thermistor, resistance temperature detector, silicon bandgap temperature sensor and any combination thereof.

It is still an object of the present invention to disclose the aforementioned system, wherein the at least one thermal data is a temperature measurement of the at least a portion of the tissue over time.

It is still an object of the present invention to disclose the aforementioned system, further comprising a step of selecting said time t to be in a range from about 10 ns to about 10 min.

It is still an object of the present invention to disclose the aforementioned system, wherein the processor is further adapted to read a computer readable medium with instructions for: calculating heat transfer index of thermal image data obtained over time; constructing a heat transfer map comprising, optionally spatial, locations of the heat transfer index over time, thereby generating a thermal diffusivity image; and identifying a designated spatial location in the thermal diffusivity image having a distinctive heat transfer index from surrounding spatial locations.

It is still an object of the present invention to disclose the aforementioned system, wherein, if a designated spatial location of the heat transfer map has the heat transfer index falling within a predetermined slope, the designated spatial location is deemed suspect of at least one irregularity in the tissue's cells.

It is still an object of the present invention to disclose the aforementioned system, wherein the spatial location is selected from the group consisting of one pixel, a plurality of pixels, a sub-pixel and any combination thereof.

It is still an object of the present invention to disclose the aforementioned system, wherein the thermal sensor is adapted to collect thermal data of at least a portion of the tissue over time, while the thermomodulating means is applied, thereby enabling the processor to calculate the heat transfer index in real-time.

It is still an object of the present invention to disclose the aforementioned system, further comprising at least one sensor selected from the group consisting of a thermometer, a hygrometer, a photodetector and any combination thereof.

It is still an object of the present invention to disclose the aforementioned system, further comprising a spatial positioning means selected from the group consisting of a visible light imaging means, a CCD camera, an ultrasound scanner, a thermal camera, a laser rangefinder and any combination thereof.

It is still an object of the present invention to disclose the aforementioned system, further comprising a mechanical speculum.

It is still an object of the present invention to disclose the aforementioned system, wherein the distinctive heat transfer index is correlated with Cervical Intraepithelial Neoplasia (CIN).

It is still an object of the present invention to disclose the aforementioned system, wherein the examined tissue is derived from a mammal selected from the group consisting of human, monkey, rodent, sheep, goat, cow, horse and swine.

It is still an object of the present invention to disclose the aforementioned system, wherein the examined tissue is selected from the group consisting of lungs, skin, cervix, ear, nose, throat, oral cavities, esophagus, stomach, intestine, colon, rectum, kidney, uterus, urinary tract, bladder, prostate, eyes, and any part of the human body.

It is still an object of the present invention to disclose the aforementioned system, further comprising a display means for presenting a graphical representation of a feature selected from the group consisting of a user interface, the heat transfer map, the heat transfer index analysis, the marking of at least one irregularity in the tissue's cells, border lines of the marking of at least one irregularity in the tissue's cells, a visual image of the examined tissue's area, the thermal data, the thermal image data, the heat diffusion image and any combination thereof.

It is still an object of the present invention to disclose the aforementioned system, wherein the display is adapted to further display data relating to patient parameters selected from the group consisting of sex, age, smoking habits, drinking habits, number of births, height, weight, blood pressure, diabetes state, medical history, relatives' medical history, patient's previous heat transfer index analysis and any combination thereof.

It is still an object of the present invention to disclose the aforementioned system, wherein the thermomodulating means are adapted to provide and/or draw heat in a manner selected from the group consisting of advection, convection, conduction, radiation and any combination thereof.

It is still an object of the present invention to disclose the aforementioned system, wherein the thermomodulating means are adapted to heat the at least a portion of the examined tissue, or cool the at least a portion of the examined tissue, or both.

It is still an object of the present invention to disclose the aforementioned system, wherein the thermomodulating means are selected from the group consisting of hot and/or cold fluid inhalation, hot and/or cold fluid application, halogen lamp exposure, LED light exposure, xenon lamp exposure, flash lamp exposure, incandescent lamp exposure, IR emission, radiation, electromagnetic and/or mechanical vibration heating, hot and/or cold solid positioning, hot and/or cold patch positioning, pharmaceutical heat modification, chemically induced heating and/or cooling and any combination thereof.

It is still an object of the present invention to disclose the aforementioned system, wherein the thermal sensor position is selected from the group consisting of mounted outside the body, inserted to the body in an invasive procedure, inserted to the body in a semi-invasive procedure and any combination thereof.

It is still an object of the present invention to disclose the aforementioned system, wherein the heat transfer index is calculated according to the thermal sensor's resolution, sampling rate and camera sensitivity.

It is still an object of the present invention to disclose the aforementioned system, wherein the examined tissue is a biopsy sampling of a tissue area suspected of having at least one irregularity in the tissue's cells.

It is still an object of the present invention to disclose the aforementioned system, wherein a second examined tissue is a biopsy sampling of a healthy tissue area, and obtained heat transfer index is compared between the suspected tissue area and the healthy tissue area.

It is still an object of the present invention to disclose the aforementioned system, wherein the heat transfer index is used for at least one of the following: detecting and mapping tumor boundaries for tumor removal operations; and determining medical severity and/or malignancy status of the at least one irregularity in the tissue's cells.

It is still an object of the present invention to disclose the aforementioned system, further comprising a database containing at least one heat transfer index of at least one second tissue, and further wherein the processor is adapted to: compare between the at least one baseline heat transfer index of at least one second examined tissue and the at least one heat transfer index of at least one examined tissue, and detect and diagnose at least one irregularity in the tissue's cells according to a difference between the baseline heat transfer index of the second tissue to the heat transfer index of the examined tissue.

It is still an object of the present invention to disclose the aforementioned system, wherein the second examined tissue is selected from the group consisting of a healthy tissue, a tissue containing at least one irregularity in the tissue's cells and any combination thereof.

It is still an object of the present invention to disclose the aforementioned system, further comprising a storing means for storing the database, selected from the group consisting of a computer readable medium, a server, a cloud-like server and any combination thereof.

It is still an object of the present invention to disclose the aforementioned system, wherein the processor is in operative communication with the storing means, optionally wirelessly.

It is also an object of the present invention to provide a computer readable medium (CRM), or electronics component, having instructions which, when implemented by one or more computers cause the one or more computers to: process thermal data derived from a thermal sensor collected over time; calculate at least one heat transfer index of the thermal data over time; wherein the heat transfer index is calculated according to a derivative of the thermal data over time.

It is still an object of the present invention to disclose the aforementioned CRM or electronics component, wherein the derivative is selected from the group consisting of first derivative, second derivative, third derivative and any combination thereof.

It is still an object of the present invention to disclose the aforementioned CRM or electronics component, further wherein the instructions which, when implemented by one or more computers cause the one or more computers to normalize the heat transfer index to a predetermined scale.

It is still an object of the present invention to disclose the aforementioned CRM or electronics component, wherein the scale is a numerical scale between 1 and 10, further wherein a higher value indicates a higher severity of the medical condition of the at least one irregularity in the tissue's cells.

It is still an object of the present invention to disclose the aforementioned CRM or electronics component, further wherein the instructions which, when implemented by one or more computers cause the one or more computers to correlate the distinctive heat transfer index with associated at least one irregularity in the tissue's cells; thereby detecting and diagnosing at least one irregularity in the tissue's cells.

It is still an object of the present invention to disclose the aforementioned CRM or electronics component, further wherein the instructions which, when implemented by one or more computers cause the one or more computers to correlate distinctive the heat transfer index with associated at least one irregularity in the tissue's cells selected from the group consisting of malignant tumors, precancerous tumors, benign tumors, infections, pneumonia, necrotic cells and any combination thereof.

It is still an object of the present invention to disclose the aforementioned CRM or electronics component, further wherein the instructions which, when implemented by one or more computers cause the one or more computers to: construct a heat transfer map comprising, optionally spatial, locations of the heat transfer index over time; and present on a display unit a designated spatial location in the heat transfer map having distinctive heat transfer index from surrounding spatial locations.

It is still an object of the present invention to disclose the aforementioned CRM or electronics component, wherein the instructions which, when implemented by one or more computers cause the one or more computers to present on a display unit a designated spatial location in the heat transfer map having distinctive heat transfer index from surrounding spatial locations, further wherein the spatial location is selected from the group consisting of one pixel, a plurality of pixels, a sub-pixel and any combination thereof.

BRIEF DESCRIPTION OF THE FIGURES

The novel features believed to be characteristics of the invention are set forth in the appended claims. The invention itself, however, as well as the preferred mode of use, further objects and advantages thereof, will best be understood by reference to the following detailed description of illustrative embodiment when read in conjunction with the accompanying drawings, wherein:

FIG. 5A illustrates the cell types and their experimental configuration, while FIG. 5B illustrates a visual demonstration of the heat transfer map of the six cell types illustrated in FIG. 5A;

FIGS. 8A-B show an example of a graphical representation of data as obtained from a cured swine meat, wherein FIG. 8A exemplifies a spatial positioning means, i.e. a camera, and FIG. 8B represents the graphical presentation of the thermal data collected by a thermal sensor;

FIG. 9 graphically illustrates temperature decay profiles of two sets of tissue cultures as presented in FIG. 5;

DETAILED DESCRIPTION OF THE PREFERRED EMBODIMENTS

Figure 1:
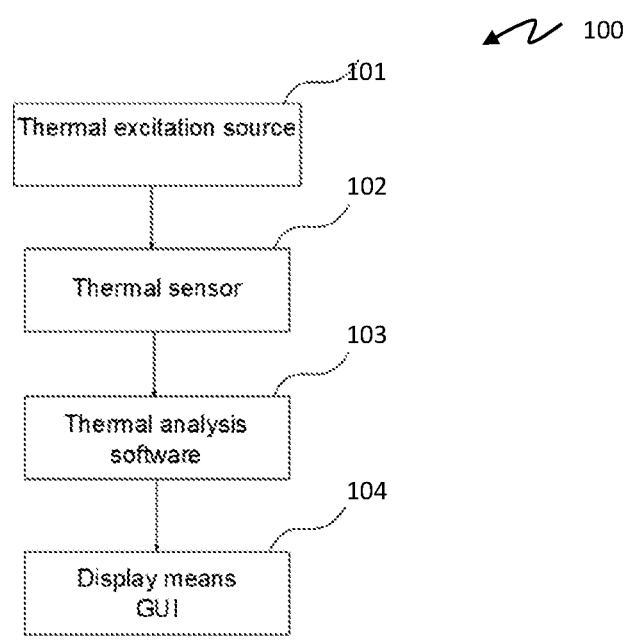
FIG. 1 presents a top level scheme of the method disclosed by the present invention.

The following description is provided, alongside all chapters of the present invention, so that to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a method for detection and diagnosis of at least one irregularity in the tissue's cells in a healthy tissue.

The term "at least one irregularity in the tissue's cells" refers hereinafter to malignant tumors, precancerous tumors, benign tumors, neoplasms, infections, pneumonia infected cells, necrotic cells, infected cells, blood clots and any other cell type exhibiting distinctive thermal transfer properties from healthy standard tissue.

The term "camera sensitivity" refers hereinafter to the capacity to have the signal stand out from the surrounding noise, i.e. the signal-to-noise ratio acquired by the camera, and in the case of a thermal sensor, this translates to the capacity to detect minute temperature differences.

The term "radiation" refers hereinafter to the use of any visible or non-visible radiation which has the capacity to elevate the temperature of the target tissue, such as emitted by, in a non-limiting manner, halogen lamp, incandescent lamp, IR emission, and pertaining to any such electromagnetic wave and non-ionizing radiation.

The term "hot" or "heating" refers hereinafter to a temperature higher than the examined tissue, or an object having a temperature higher than the examined tissue.

The term "cold" or "cooling" refers hereinafter to a temperature lower than 37° C., or an object having a temperature lower than 37° C.

The term "fluid" refers hereinafter to a liquid or a gas, which may be hot or cold, and may refer to in a non-limiting example to atmospheric air, oxygen, nitrogen, helium, hydrogen, carbon dioxide, steam, water or oil.

The term "spatial positioner" refers hereinafter to any imaging device providing information with regards to the physical position of the examined tissue, and may include visible-light imaging means, such as a CCD camera, a laser rangefinder, an ultrasound scanner and so forth, resulting in a spatial image of the examined tissue's area. Spatial positioning means may give out results in a one dimensional output, two dimensional or three dimensional output.

The term "thermal data" refers hereinafter to any numerical or image-like data depicting the temperature of at least a portion of an examined tissue.

The term "thermal image data" refers hereinafter to a visual representation of thermal data in the form of a digital image.

The term "heat transfer map" refers hereinafter to thermal image data depicting the change in temperature of at least a portion of an examined tissue over time.

The term "heat diffusion image" refers hereinafter to an image depicting the thermal diffusivity of at least a portion of an examined tissue over time.

The term "heat transfer index" refers hereinafter to the rate of heat transfer exhibited by at least a portion of an examined tissue after being exposed to active thermoregulation.

The term "tissue" refers hereinafter to any of a tissue culture, a cell line, a biopsy sampling, an in situ tissue (i.e. in the examined animal) and the like.

The term "thermomodulating means" refers hereinafter to any means or method for heating or cooling a tissue.

The present invention exploits active thermography to identify minute variations between healthy tissues as compared to tissues undergoing cancerous/precancerous stages, or any other irregularity in at least one cell of the examined tissue. Active thermography is the induction of a heat flow by energetically exciting a test object. The heat flow is influenced by interior material layers and defects. These inhomogeneities can be captured on the surface by high-precision thermal sensors. The inventors of the present invention have discovered that even a minor differentiation of tissue cells, such as in precancerous conditions, results in biomechanical-thermal differences which lead to differences in heat flow, and therefore to a distinctive thermal diffusivity and heat transfer.

Reference is now made to FIG. 1 illustrating a top level overview of the core technological features of the present invention's system 100. Thermal excitation source 101, or thermomodulating means, is first used on an examined tissue. The thermal excitation may be through transferring heat to the tissue by any energy inducing device or through drawing heat from the tissue through exposure to cold objects, or by any pharmaceutical administration altering body temperature, or by any chemical reaction configured to induce temperature alterations in any part of the body. After such thermal excitation, heat transfer is induced throughout the tissue. The heat transfer is dependent on the thermal diffusivity properties of the tissue, such that healthy tissue has certain thermal diffusivity properties and tissues having at least one irregularity in the tissue's cells exhibit distinctive thermal diffusivity properties. Heat transfer may be the result of advection, convection, conduction, radiation and may be carried out by any device or means such as, in a non-limiting example, hot and/or cold fluid inhalation, hot and/or cold fluid application, halogen lamp exposure, LED light exposure, xenon lamp exposure, flash lamp exposure, incandescent lamp exposure, IR emission, radiation, electromagnetic and/or mechanical vibration heating, hot and/or cold solid positioning, hot and/or cold patch positioning, pharmaceutical heat modification, chemically induced heating and/or cooling and any combination thereof.

In various embodiments of the present invention, the examined tissue may be at least a section of a tissue in an examined individual. Such individual may be any mammal, such as in a non-limiting example, human, monkey, rodent, sheep, goat, cow, horse and swine, and may be derived from any body part, including in a non-limiting example, lungs, skin, cervix, ear, nose, throat, oral cavities, esophagus, stomach, intestine, colon, rectum, kidney, uterus, urinary tract, bladder, prostate and eyes. Preferably, the examined body part is of a kind that is accessible to thermal excitation and thermal sensing.

In other embodiments of the present invention, the examined tissue may be an in vitro examined biopsy sample taken from at least a section of a tissue of an examined individual. The biopsy sample may be healthy tissue or tissue suspected of having at least one irregularity in the tissue's cells. And yet in other embodiments, the examined tissue may be an extracted cell line or cell culture grown on a dish.

In preferred embodiments the examined tissue is human cervix tissue examined in situ i.e. in the patient himself, and the resultant identified at least one irregularity in the tissue's cells are Cervical Intraepithelial Neoplasia (CIN). However, at least one irregularity in the tissue's cells may also refer to any cancerous or precancerous tissues found in any other part of the examined body.

The heat transfer is monitored with thermal sensor 102, which is preferred to be an IR camera or IR sensor, but may be any sensor which could provide thermal data, which is preferably temperature values. Other sensors which may be used are an ultrasound temperature sensor, a mercury-in-glass thermometer, a pill thermometer, a liquid crystal thermometer, a thermocouple, a thermistor, a resistance temperature detector, a silicon bandgap temperature sensor and any combination thereof. In some embodiments, the thermal sensor produces thermal data which consists of a series of time-resolved temperature measurements. In other embodiments, thermal sensor 102 can produce a plurality of time-resolved thermal image data, or thermal digital images, preferably over a time interval in a range from about 10 ns to about 10 min. Thermal sensor 102 may be mounted outside the body or inserted into the body in an invasive procedure, or in a semi-invasive procedure.

Thermal data, or thermal image data is then transferred to a processor comprising thermal analysis software 103. This processor is found in operative communication with thermal sensor 102, optionally through wireless communication.

In some embodiments, the thermal analysis software 103 can contain instructions for calculating the heat transfer index, i.e. the rate in which the heat transferred through the examined tissue, according to the thermal data, or thermal image data taken over time. These calculations include deriving the derivative of the change in the thermal data detected over time. The derivative may be a first derivative, a second derivative or a third derivative of the thermal data, or thermal image data (through spatial location intensity derivation), and any combination thereof. A plurality of such heat transfer indexes may be then used to construct a heat transfer map exhibiting these temporal heat transfer indexes through spatial locations, which may be at a single pixel resolution, a plurality of pixel resolution or sub-pixel resolution, which is less than one pixel, i.e. super-resolution. Optionally, binning is used to illustrate the heat transfer index, i.e. through spatial locations which comprise a plurality of pixels. At least one irregularity in the tissue's cells are identified by identifying a designated spatial location having a distinctive heat transfer index from its surrounding spatial locations. At least one irregularity in the tissue's cells may also be detected or diagnosed through suspected heat transfer index, or heat transfer index which is found within a known heat transfer range to be suspected of at least one irregularity in the tissue's cells.

In some embodiments, thermal analysis software 103 calculates the heat transfer index through an algorithm comprising first measuring the intensity of each of the spatial locations, followed by determining a first derivative of the measured intensity over time, and finally determining the heat transfer index according to the first derivative. In an embodiment of the present invention, a second or third derivative of the intensity over time may be used to calculate the heat transfer index. In various embodiments the heat transfer index is calculated in accordance with the thermal sensor's resolution, sampling rate and sensitivity.

In some embodiments, the thermal analysis software 103 contains instructions for calculating the thermal rate index, which may be in some embodiments the thermal transfer rate constant, i.e. the typical time it takes for the active thermo-modulation to decay or recover in a specific tissue region, for each of the coordinated locations. Each tissue type, depending on its unique composition and metabolic activity, exhibits a different rate constant. This means that coordinated locations comprising portions of the tissue having at least one irregularity in the tissue's cells, will exhibit a thermal rate constant which is different from the surrounding, other healthy portions of the tissue. It is thus disclosed by the present invention that determining the rate in which active thermal modulation equilibrates over time in various tissues reveals nuances and differences between such tissues, which may not be detected using a different stimulation, detection or analysis. A plurality of such thermal rate indexes may then be used to construct a visual presentation, in the form of a map, exhibiting these temporal thermal rate differences according to the coordinated locations, which may be at a single pixel resolution, a plurality of pixel resolution or sub-pixel resolution, which is less than one pixel, i.e. super-resolution, or may comprise a single cell resolution, or a plurality of cells. Optionally, binning is used to illustrate the thermal rate constants, i.e. through averaging spatial locations which comprise a plurality of pixels. At least one irregularity in the tissue's cells are diagnosed by identifying a designated spatial, i.e. coordinated, location having a distinctive thermal rate index from its surrounding spatial locations. At least one irregularity in the tissue's cells may also be detected or diagnosed through thermal rate constants which are found within a known range suspected of relating to at least one irregularity in the tissue's cells.

The thermal transfer index, I, is used to obtain a threshold value which will be correlated with a predetermined value $I_{irr}$, establishing a diagnosis. The index I may be directly correlated to the value $I_{irr}$, or it may be normalized by a scale value $I_{scale}$. In various embodiments, I is calculated for at least two distinct coordinated locations, and then a first calculated $I_{first}$ is normalized to a second calculated $I_{second}$, and the result is then compared to $I_{irr}$.

In various other embodiments, the thermal transfer index is defined according to the formula of $T=a+b*\exp(-I*t)$, where a and b are constants, T is the temperature and t is the time over which the thermal data was collected.

In various embodiments of the present invention, the thermal rate index is not used directly in constructing the heat map, or visual presentation, but an inferential thereof is used. Such inferential value is derived from the thermal rate index in some kind of a mathematical manipulation and may lead to important metabolic parameters such as thermal conductivity coefficient, thermal diffusion coefficient, heat capacity, density, heat loss due to blood perfusion, blood temperature, heat convection index, metabolic heat source and any combination thereof.

In order to construct the visual presentation, or heat map, the thermal rate constant, or an inferential thereof, is normalized to a predetermined numerical scale, which is pre-associated with color, or pixel intensity, or both. In some embodiments, the scale is a numerical scale of between 1 and 10, wherein 1 could represent healthy cells or 1 could represent the most severe case of at least one irregularity in the tissue's cells. Such a scale should provide the practitioner using the system and method of the present invention with a tool for outlining the boundary of the malignant tissue, by means of the map, and also for estimating the severity of the condition. Use of the tool can assist a practitioner to determine a more optimal treatment of the irregularity.

In preferred embodiments, thermal analysis software 103 calculates the thermal rate constant through an algorithm comprising first measuring the intensity of each of the spatial locations, and following the intensity modification over time, and finally extracting the thermal rate constant, usually by finding the exponential decay constant of the measured heat decay profile. In various embodiments of the present invention, the thermal rate constant may be a heat decay rate detected after heating, or it may be a heat recovery rate detected after cooling. In various embodiments the thermal rate constant is calculated in accordance with the thermal sensor's resolution, sampling rate and sensitivity.

In some embodiments, thermal sensor 102 is operated during the heating and/or cooling applied by thermal excitation source 101, and consequently, thermal analysis software 103 is configured to calculate the thermal diffusion through the examined tissue, as a consequence of the application of thermal sensor 101, in real-time.

In various embodiments, the heat transfer index is normalized against personal patient parameters such as, in a non-limiting example, sex, age, smoking habits, drinking habits, number of births, height, weight, blood pressure, diabetes state, medical history, relative's medical history, the patient's own previous heat transfer index analysis and any combination thereof.

In an embodiment of the present invention, the heat transfer map's emerging markings of distinctive heat transfer indexes is used for detecting and mapping the at least one irregularity in the tissue's cells' borders and for surgical removal of the markings findings.

Results of thermal analysis software 103 are then displayed on display means 104 comprising a user interface. The display means may be a monitor which is part of the system, or of a personal computer or the screen of any other electronic device such as a personal tablet, smartphone, smart TV and the like. The electronic device may comprise the thermal analysis software 103 in itself or may be in operative communication with the processor comprising thermal analysis software 103, wirelessly or through wire communication.

At least one irregularity in the tissue's cells may be recognized by correlating the emerging heat transfer index with associated at least one irregularity in the tissue's cells, which may be selected from a group consisting of a malignant tumor, a precancerous tumor, a benign tumor, infections, pneumonia, a necrotic cell, a blood clot and any combination thereof. At least one irregularity in the tissue's cells may also be recognized by comparing the emerging heat transfer indexes to a predetermined range of slopes which are suspected to be the result of irregular biomechanical-thermal properties in a tissue. In other embodiments, the heat transfer indexes may be compared to a baseline of healthy tissues or other tissues comprising at least one irregularity in the tissue's cells, whether extracted from the same patient or from a plurality of other examined individuals.

In several embodiments, thermal analysis software 103 is configured to calculate a ratio between the distinctive heat transfer index of the suspected area to the heat transfer index of the surrounding tissue area. This ratio can then be compared to other ratios taken from other examined individuals.

Display means 104 may illustrate a numerical or graphical presentation of the gradient temperatures, the heat transfer maps, the thermal data images, at least one irregularity in the tissue's cells markings, at least one irregularity in the tissue's cells border, the patient's personal parameters and the like.

The procedure includes heating and/or cooling application to the examined area, forcing the tissue to transfer heat, followed by monitoring the tissue's heat transfer and cooling by a thermal sensor screening sampling of multiple thermal images, until full coverage of examined tissue surface is reached, and finally constructing temperature profile in relation to time and location, as measured during the test (marking any irregularities).

In some embodiments, the device is directed to examining the lungs. In such an embodiment, heat convection by inhalation of hot gas, such as atmospheric air, oxygen, helium, hydrogen, nitrogen, carbon dioxide or any other inhalable gas would supply a heat application to at least a portion of the lung area, from the symphonies to the alveolus. The thermal potential created between the surface lung tissues and the internal ones would transfer heat to the inner tissues. There, it would be absorbed and spread by the internal layers. This is done due to several heat transfer mechanisms found in biological tissues and conduction. This process would eventually balance at steady state. Since cancerous tissues vary in thermal properties from healthy ones and specifically the thermal diffusion, it would stand out of the healthy environment. Using the thermal camera images taken throughout the procedure, heat transfer index analysis is made. Area temperature mapping (According to the camera's resolution), at different times (according to the camera's sampling rate—FPS) is depicted. This maps the diffusion properties, revealing the abnormal areas. Finally a three dimensional map of the examined tissue or organ is constructed, marking the suspected areas.

Figure 2:
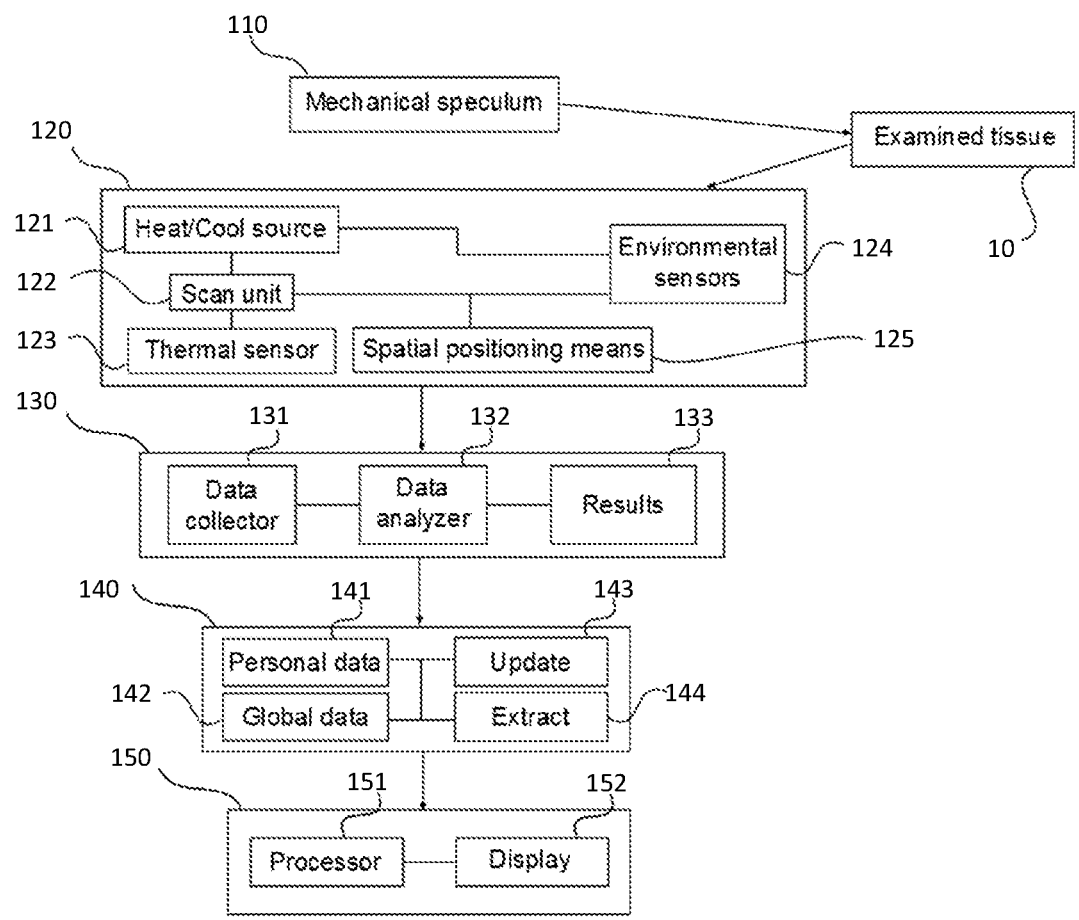
FIG. 2 schematically presents high level overview of a preferred embodiment of the system disclosed by the present invention.

Reference is now made to FIG. 2, illustrating a high level overview of a preferred embodiment of the system disclosed by the present invention. The system disclosed by the present invention may comprise mechanical speculum 110, in order to gain access to examined tissue 10 which me be an inner tissue area, such as the cervix. After gaining access to examined tissue 10, scanner module 120 is operated. The module comprises a heat/cool source 121, scan unit 122, thermal sensor 123, and may further comprise spatial positioning means 125, which could be in a non-limiting example a CCD camera, a thermal camera, a laser rangefinder, or an ultrasound scanner, and may also comprise at least one environmental sensor adapted to measure various parameters of the ambient environment where the examination takes place, and this sensor may be, in a non-limiting example a thermometer, a hygrometer, a photodetector and any combination thereof.

In an embodiment of the present invention, the heat/cool source 121 could be any device which is configured to apply heat to the surface area of an examined tissue in a manner of advection, convection, conduction, radiation or any combination thereof. In a similar manner, cooling may be conducted by using a device which is configured to remove heat from the surface area of the tissue, in the manner of advection, convection, conduction, radiation or any combination thereof. Radiation may be applied in any wave length.

Thermal sensor 123 refers to any device providing detection of thermal energy in a resolution of time and space, and producing thermal image data. Preferably, thermal sensor 123 is an IR sensor, but not limited to it, and thermal sensor 123 may also be a mercury-in-glass thermometer, pill thermometer, liquid crystal thermometer, thermocouple, thermistor, resistance temperature detector, silicon bandgap temperature sensor and any combination thereof.

In some embodiments, thermal image data can be image processed by an object recognition module, it can be correlated with data from other imaging modalities and any combination thereof. The other imaging modality can be, but not limited to, a camera image, a CT scan image, an MRI image, an ultrasound image, and any combination thereof. By this means, coordinated locations suspected of containing at least one irregularity in the tissue's cells can be more accurately identified. In some embodiments, the system can correlate at least one thermal image and at least one image from at least one spatial positioner to better identify the locations of any irregularities.

Thermal image data and any other data is then communicated to the software module 130, which comprises data collector submodule 131, data analyzer submodule 132 and results submodule 133. Software module 130 comprises the thermal analysis software 103 and results in temperature measurements which are subjected to mathematical manipulations including deriving a first, second or third derivative of the change in temperature over time, resulting in the heat transfer index. This index may further be used to construct the heat transfer map or the thermal diffusivity image exhibiting the suspected areas of at least one irregularity in the tissue's cells. Data collector 131 is found in operative communication with scanner module 120, and comprises all the data available from module 120. Data analyzer 132 is found in communication with data collector 131 and extracts the relevant data required for the heat transfer index analysis. Results 133 is found in communication with data analyzer 132 and contains analyzed data from cervical scanner 120.

In some embodiments, image processing by an object recognition module, correlation with images from other modalities and any combination thereof can be done with the thermal diffusivity image.

The results 133 data, the analysis data of data analyzer 132 and the raw data of data collector 131 are then preferably transferred to database 140. This database may be found in the same electronic device as software module 130, or may be in a different device, and even possibly, the data is wirelessly transmitted to database 140 which is found at a different location. Database 140 may comprise various submodules, and in the illustrated embodiment it comprises personal data submodule 141, global data submodule 142, update submodule 143 and extract submodule 144.

Personal data 141 comprises personal patient parameters which may contain sex, age, smoking habits, drinking habits, number of births, height, weight, blood pressure, diabetes state, medical history, relatives' medical history, patient's previous heat transfer index and any combination thereof Global data 142 may comprise data relating to examined tissues or organs in other tissues and/or in other individuals. Preferably global data 142 contains a database of examinations of a plurality of tissues (a plurality of tissues from a single individual, or a plurality of tissues from a plurality of individuals whose data has been recorded), according to the method as recited in the present invention. This database collectively provides a heat transfer index baseline according to which an immediate examination is referred to. Global data 142 may comprise raw data taken from the scanner module, at least partially analyzed data and/or results data. It may also contain personal information related to the examined individuals participating in the baseline database. Preferably, global data provides the ratio between healthy tissues and tissues exhibiting at least one irregularity in the tissue's cells. The ratio may then be compared between the patient and a database containing such ratios from other examinees. The comparison between the patient's ratio and the global data's ratios will enable a better identification of the irregularity in the tissue's cells, as well as the severity of the medical condition and the malignancy status.

Update 143 provides an updated analysis of the heat transfer index results 133 derived from scanner module 120, in view of the baseline data of global data 142. Extract 144 provides the finalized analysis of the heat transfer index results, after being compared to the baseline data. The baseline gradient temperature may refer to healthy tissues, or may refer to any tissue having at least one irregularity in the tissue's cells. Global data 142 may comprise a plurality of databases relating to various tissue conditions, and comparison to the appropriate database may be determined, inter alia, according to personal data 141.

The final results of the analyzed tissue heat transfer provided by database module 140 are then transferred to the user interface module 150, which preferably comprises processor 151 and display 152. User interface 150 enables both data representation and data input by a user, where user of the system provided by the present invention enters any data which is relevant to the analysis of the heat transfer index. In addition, the user may decide which output will be presented to him on the display and in which manner.

Figure 3:
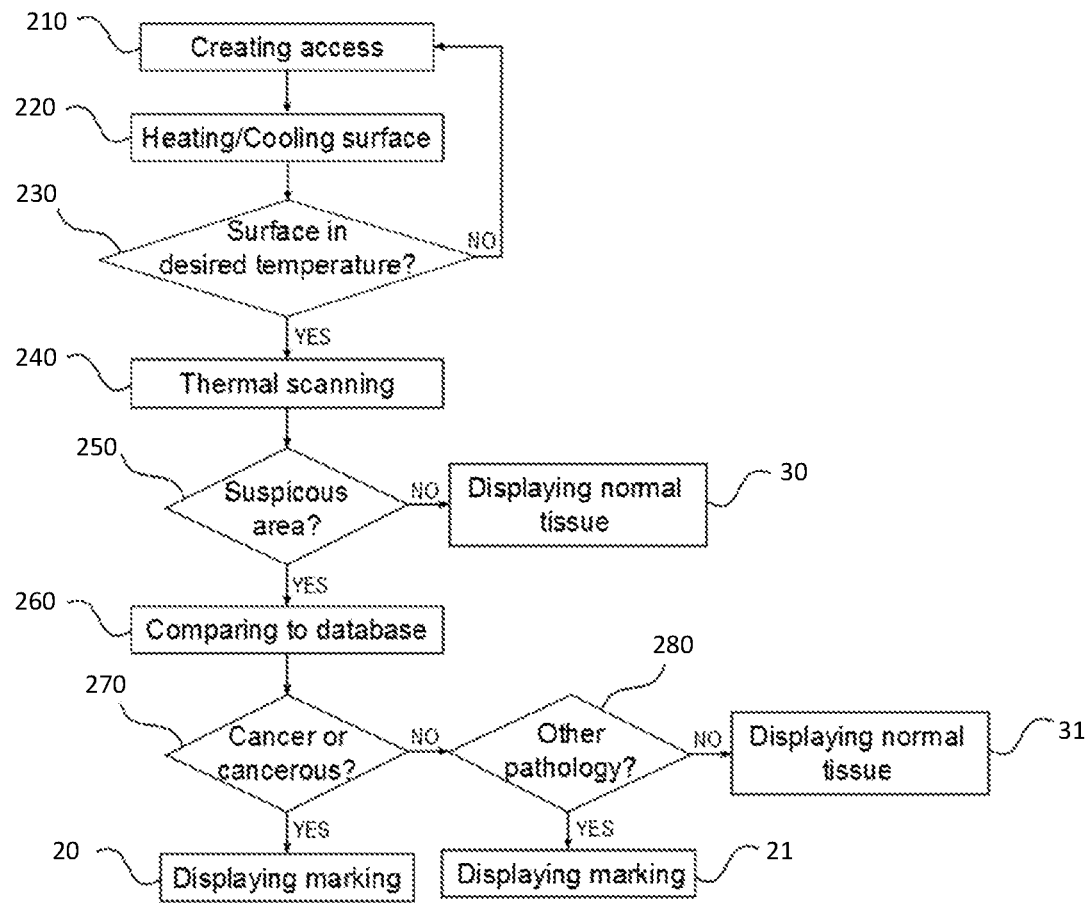
FIG. 3 schematically presents a high level overview of a preferred embodiment of the method disclosed by the present invention.

Reference is now made to FIG. 3, illustrating a high level overview of a preferred embodiment of the method disclosed by the present invention. Preferably the method is conducted on the examined individual, if needed by creating access 210 to the suspected tissue, using device such as, in a non-limiting example, a mechanical speculum. After gaining access to the suspected area, at least a portion of its surface undergoes heating and/or cooling 220. The elevation/reduction in tissue temperature is monitored and if the temperature has not reached the desired value 230, then a better access 210 and/or re-heating/cooling 220 is repeated. If the temperature has reached the desired value, then thermal scanning 240 is conducted next.

Thermal scanning 240 includes the use of a thermal sensor, such as preferably an IR sensor, but could also include a mercury-in-glass thermometer, pill thermometer, liquid crystal thermometer, thermocouple, thermistor, resistance temperature detector, silicon bandgap temperature sensor and any combination thereof, and the heat transfer index analysis, resulting in a heat transfer map. If no distinctive heat transfer indexes emerge 250, i.e. the heat transfer map is homogenous and normal tissue status is displayed 30, showing a numerical or graphical representation of healthy results. If on the other hand, inhomogeneous regions are suspected to be in the heat transfer map, the data is preferably compared to a database 260. The database comprises a baseline derived from various examinations of other tissues and/or other examined individuals, as depicted in FIG. 2. According to the comparison 260, it can be determined if the tissue is cancerous/precancerous 270, in addition to providing an estimate of the severity of the medical condition, the extent of at least one irregularity in the tissue's cells or the malignancy status of the tumor. Such a comparison may be to the heat transfer index itself, or to the ratio between the heat transfer index exhibited by the healthy tissue to the heat transfer index exhibited by the suspicious tissue. If it is, then marking is displayed for the cancerous region 20. If the comparison does not result in cancer suspicious tissue, other pathologies may be diagnosed 280, might be with the use of other baselines. If other pathologies are identifies, then markings of the found pathological region is displayed 21. If no cancer, and no other pathology are found, then normal tissue status is displayed 31.

In some embodiments of the system, at least one map of the examined area is generated. The map can be a two-dimensional map of a narrow region, a slice of the subject, or a three-dimensional map of a portion of a subject. The map can be of at least one tissue parameter or of a time-resolved tissue parameter, where the tissue parameter can be selected from a group consisting of: thermal conductivity coefficient, thermal diffusion coefficient, heat capacity, density, heat loss due to blood perfusion, blood temperature, heat convection index, metabolic heat source and any combination thereof. At least one map can be of the analyzed time-resolved thermal data, for example by color-mapping the resultant time resolved thermal index, I.

According to an embodiment of the present invention, the method can also be applied to diagnosis based on comparison of the analyzed results to a baseline. This baseline could be any tissue which was processed using the method proposed in the present invention, i.e. any healthy or malignant tissue, which has been applied with heating or cooling, and been scanned for temperature gradient profiling. The temperature gradient profile, and the resulting heat transfer index, of the examined tissue can be compared with the temperature gradient profile, and the resulting heat transfer index, of the baseline tissue. Identification of similar patterns will enhance the likelihood of correct diagnosis and, therefore, selection of suitable treatment routines.

In various embodiments of the present invention, the heat transfer index is normalized to provide a scale, preferably a numerical scale, which has a range between 1 and 10, wherein a higher value indicates a higher severity of the medical condition of an irregularity in the tissue's cells, or a later cancer stage. A value of 0 may indicate healthy tissue.

Figures 4, 5A, 5B:
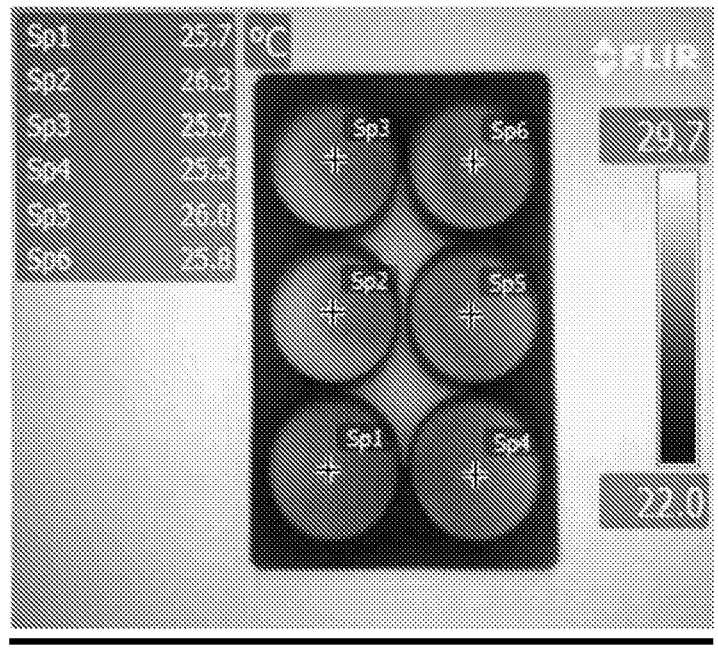
FIG. 4 presents the cell types examined under the present invention and their index numbers.
FIG. 5A-B illustrates a first experimental setup using six cell types for examination.

Reference is now made to FIGS. 4-7, demonstrating results of a first experimental set up which includes six experiments conducted on six cell types cultures. Various cell types are compared with regards to their thermal properties. As shown in FIG. 4, the compared cell types are: lung tissue, including normal tissue (fibroblasts) and two types of cancerous tissue (H1299 and 549) and kidney tissue, both normal tissue (AK-epithelial cells) and cancerous tissue (Wilm's tumor from exografts).

FIG. 5A shows the locations on the plates of FIG. 5B of the cells of the types listed above and in FIG. 4, while FIG. 5B shows an example of the temperatures of the cells on the plates during cooling.

Figure 6:
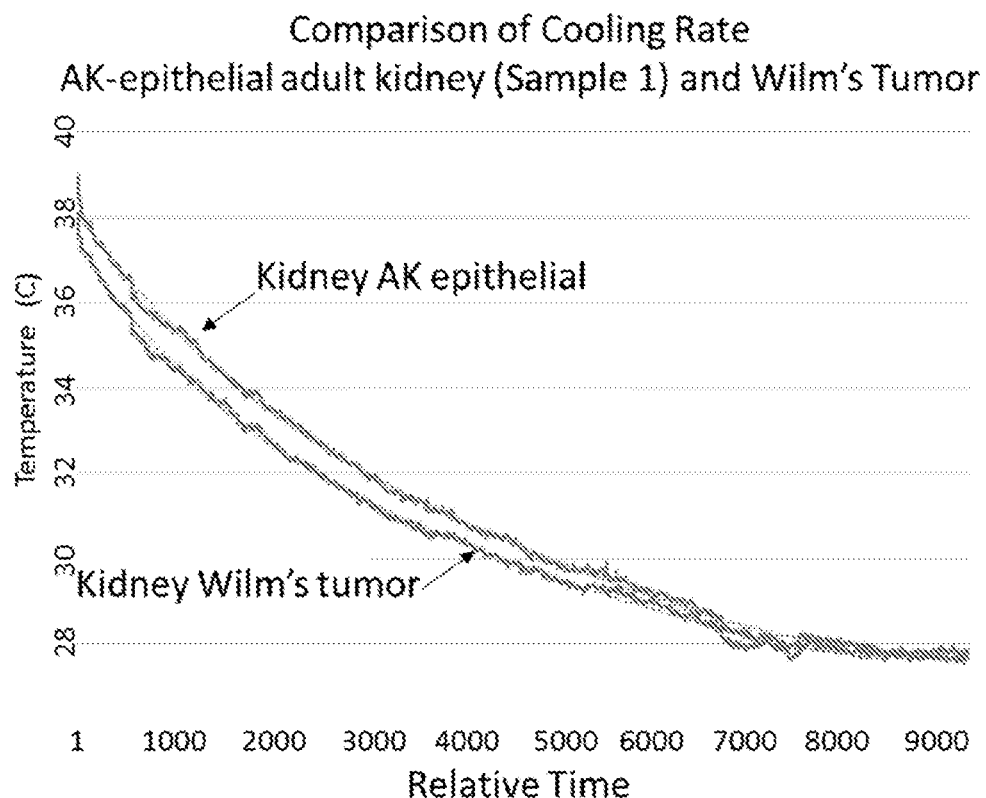
FIG. 6 graphically illustrates temperature decay profiles of the examined cell populations presented in FIGS. 5A and B.
Figure 7:
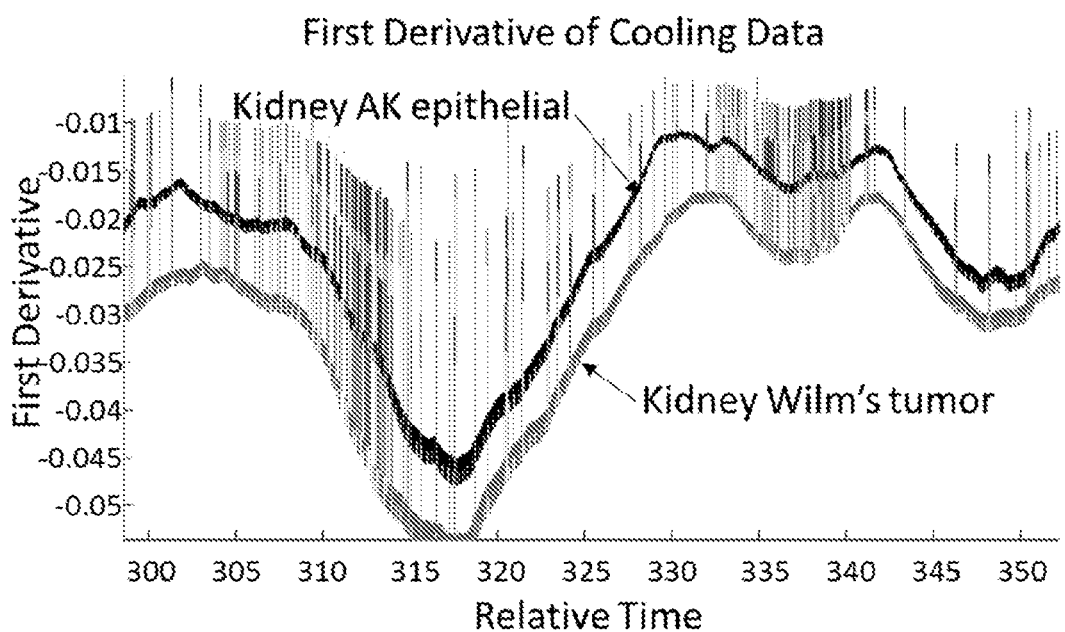
FIG. 7 graphically illustrates the first derivative of the data presented in FIG. 6.

FIG. 6 shows the differential cooling of the normal kidney tissue (upper curve) vs. the Wilm's tumor tissue (lower curve). The normal tissue both heats more and cools faster than the Wilm's tumor tissue. FIG. 7 shows the first differential of the curves in FIG. 6, where the upper curve is for the normal tissue and the lower curve for the Wilm's tumor tissue.

FIG. 8 exemplifies the data obtained and analyzed, as collected over a tissue taken from cured swine meat. FIG. 8A shows an image obtained by spatial positioner, i.e. a camera, while FIG. 8B illustrates thermal data collected by a thermal sensor, in this example an IR sensor. The image shows the analyzed time-resolved thermal data by color-mapping the resultant time resolved thermal index, I. Background has been removed by setting a threshold index I to present. The index I was calculated according to the following:

$$T = a + b*\exp(-I*t)$$

where a and b are constants and T is temperature.

The graphical presentation shows a proof of concept, illustrating the high power of the algorithm disclosed by the present application in distinguishing between tissues by exploiting their recovery from active thermomodulation.

FIG. 9 presents thermal decay profiles of two coordinated locations, one having a cancerous cell sample and the other having a healthy cell sample, illustrating that the difference in the apparent decay trend and in the calculated decay rate constant is significant. In this example, the decaying temperature measurements were fitted to the following formulas:

$$T_1(t) = 29.24 + (14.74*\exp(-0.0148*t))$$

$$T_2(t) = 29.06 + (12.91*\exp(-0.0135*t))$$

where $T_1$ gives the temperature decay curve for the normal tissue and $T_2$ gives the temperature decay curve for the cancerous tissue, with the cancerous tissue, which is cooler than the normal tissue, returning to ambient more slowly than the cancerous tissue. Thus, a significant difference between the index, $I_1$, of $T_1$ and the index, $I_2$, of $T_2$ is shown as:

$$I_1/I_2 = (-0.0148/-0.0135) = 1.09$$

i.e. approximately a 10% difference. This example illustrates that a calculated ratio between two thermal transfer indexes I, which is greater than $I_{irr} = 10\%$ corresponds with an irregularity in the tissue's cells.

The tested tissue is thermally excited by heating or cooling the tissue surface, and is then carefully monitored for heat spread and absorption. Using infrared sensors, thermal surface images are obtained in various time intervals. Analyzing the temperature variation from the images, in relation to time and position can reveal points of irregularity, which suggest pathological tissue.

Without wishing to be bound by theory, the concept of using thermal analysis based on thermal diffusivity changes for finding any irregularities is already successfully implemented in the field of material analysis. Industrial and research facilities apply non-destructive tests (NDT) for a variety of materials (such as metals, polymers, concrete, composite materials and others) using infrared active analysis. The tested material is thermally excited by heating the surface, and carefully monitored for heat conduction. Using infrared sensors, thermal surface images are obtained for different sampling times. Analyzing the temperature profile from the images, in relation to time and position can reveal irregularities. These might be cracks or any other flaws in the material, which are discovered due to differences in their thermal properties compared to homogeneous material.

Hereby is the "Penne's equation", a widely accepted temperature profiling equation for biological tissues:

$$\rho C \frac{\partial T}{\partial t} = \nabla(k \nabla T) + q + A_0 - b(T - T_b)$$

where:

$$q \left[ \frac{W}{m^3} \right]$$

External heat source;

$$A_0 \left[ \frac{W}{m^3} \right]$$

Metabolic heat source $$b \left[ \frac{W}{m^3 \, °C.} \right]$$

Heat loss due to blood perfusion; $T_b$ [° C.]—Blood temperature
T [° C.]—Tissue temperature;

$$\rho \left[ \frac{kg}{m^3} \right]$$

Density $$C \left[ \frac{J}{kg \, °C.} \right]$$

Heat capacity;

$$k \left[ \frac{W}{m \, °C.} \right]$$

Thermal conductivity factor

Biological tissues behave much like a homogenous solid whose thermal properties are defined mostly by its water content. In addition, there is a dependency of the properties on tissue temperature.

Different studies have shown that there is a temperature rise of approximately 1 degree Celsius in cancer tumor compared a healthy neighboring tissue. This is due to enhanced metabolic activity, accelerated growth mechanisms and massive blood vessel usage of the tumor. It is therefore expected to find a temperature of 380 Celsius in a lung tumor opposed to normal 37 Celsius in normal lung tissue. This change of temperature supports the premises that cancer cells have different thermal properties. This of course enables the diagnostic of such cells using active thermal imaging.

Studies include "Modeling Temperature in a Breast Cancer Tumor for Ultrasound-Based Hyperthermia Treatment" by Brian Ho et al.; Strom et al., Cancer research, 1979;

"Introduction to NDT by Active Infrared Thermography" by X. Maldague; "Thermal Properties" by Holmes; and "Tissue Thermal Properties and Perfusion" by Jonathan W. Valvano, which are incorporated herein as a reference.

The thermal conductivity factor "k" for human tissues has been tested before, however, it was not categorized to different lung tissues groups. Moreover the data that do exist does not mention the lung tissue type tested. As in many human tissues, the lung tissue contains a large amount of water. This makes its thermal properties very close to those of water and in particular the conductivity factor.

According to McIntosh and Anderson's literature survey taken in 2010, in which several conductivity factor where tested (McIntosh and Anderson, Biophysical Reviews and Letters, 2010, incorporated herein as a reference), average values can be calculated for the factor. It is hereby presented:

$$\text{Maximum value: } 0.28 \left[ \frac{W}{m\,°C.} \right]$$

$$\text{Minimum value: } 0.48 \left[ \frac{W}{m\,°C.} \right]$$

$$\text{Avrage value: } 0.38 \left[ \frac{W}{m\,°C.} \right]$$

The lung's "K" factor varies significantly according to the subject's age. Values could change from 0.3 in a child's to 0.55 in a grown man with a lung disease.

The thermal diffusion is a property subjected to changes according to the three previously mentioned properties in this manner:

$$\alpha = \frac{K}{\rho C}$$

Whereas:

$$\rho \left[ \frac{kg}{m^3} \right]$$

Density;

$$C \left[ \frac{J}{kg\,°C.} \right]$$

Heat capacity;

$$k \left[ \frac{W}{m\,°C.} \right]$$

Thermal conductivity factor

The experiment is to prove the differences in thermal diffusion between a healthy tissue and a cancer one, and that it is large enough to be successfully identified as an irregularity.

Example 1

The experimental set up used to evaluate the invention is comprised of two stages. The second stage is designed to achieve greater accuracy and elaboration of the results obtained in the first stage, in addition to handling experimental issues and difficulties arising in the first experimental stage. The second stage was conducted in view of the results obtained in the first. Experimental design goes as follows:

Image capturing of all cell cultures; Laboratory conditions take into account: (a) Neutralizing disturbances; (b) Constant temperature, registration of any alterations. (c) Registration of humidity values.

Camera set up: Control set up—heating; Control set up—cooling; Conduct experiments using heating; Conduct experiments using cooling.

Example 2

The system of the present invention can be configured as a 'decision support' system, informing a user such as a clinician as to whether a positive CT result is a cancer (true positive) and requires further investigation, or whether the positive CT result is a false positive.

With the system of the present invention, the results are immediate, do not involve radiation risks and are independent of an expert's eye. The test is computerized and automatic, with no need for a long, expensive analyzing stage.

As disclosed above, the technology is based upon analysis of the temperature decay profile and measurement of heat diffusion in the lung. It is well known that the density of cancerous cells is higher than that of normal cells, their shape is different and their nuclei are enlarged. These differences cause a fundamental change in the thermal properties of the cells. The planned operating principle—short heating followed by tracking diffusion of heat into the tissue and absorption of heat in the tissue.

An IR camera can be directed through the tumor from outside the body (or from the inside of the lung) and can be scanned during the examination. Thermal excitation can be provided by inhalation of a hot gas, such as hot hot gas, such as atmospheric air, oxygen, helium, hydrogen, nitrogen, carbon dioxide or any other inhalable gas, from a dedicated balloon, by irradiating the tissue by light (such as, but not limited to, infrared light, visible light or ultraviaolet light), or both. After application of the heat, the heat source can be deactivated and, from that moment, video images can be taken at a high acquisition rate for several minutes. During this time, the tissues will cool to a temperature close to their default, unheated, temperatures.

An analysis of the temperature decay profile at every point on the surface can be executed in real time or after a delay. For non-limiting example, the analysis can take place after data acquisition is complete. Preferably, any delay in analysis will be short, typically no more than a few minutes. A comparison can be carried out between adjacent points in the image (according to the number of pixels) and a further comparison for the database can be collected. The measurements can be processed to create a map that will mark suspected cancerous areas, if any, on a display.

The method comprises testing the tissues' response to thermal excitation over a short period of time, and therefore can distinguish between cancer and other pathologies such as benign growths or necrosis as a result of cancer treatment and surgical removal.

The evaluation can be performed with high precision because the test searches for discontinuities on a continuous surface pursuant to heat transfer in the tissues.

Unlike alternatives currently available, the test does not expose a patient to harmful radiation, can reduce the quantity of false positive/false negative results obtained and will save the health system time and money as there is no need for a medical specialist to perform the test or for an expert to decode the results.

The system's principal components:
A dedicated inhaled excitation device.
An IR camera, either outside the body or inside the lungs.
A decoding system, which includes both software and a user interface.
Optionally, a central server including a cumulative database related to the patient's medical records, to which new data can be added and re-analysis of the data can be carried out to provide improved and updated diagnosis on a timely basis.

Example 3

Figure 10:
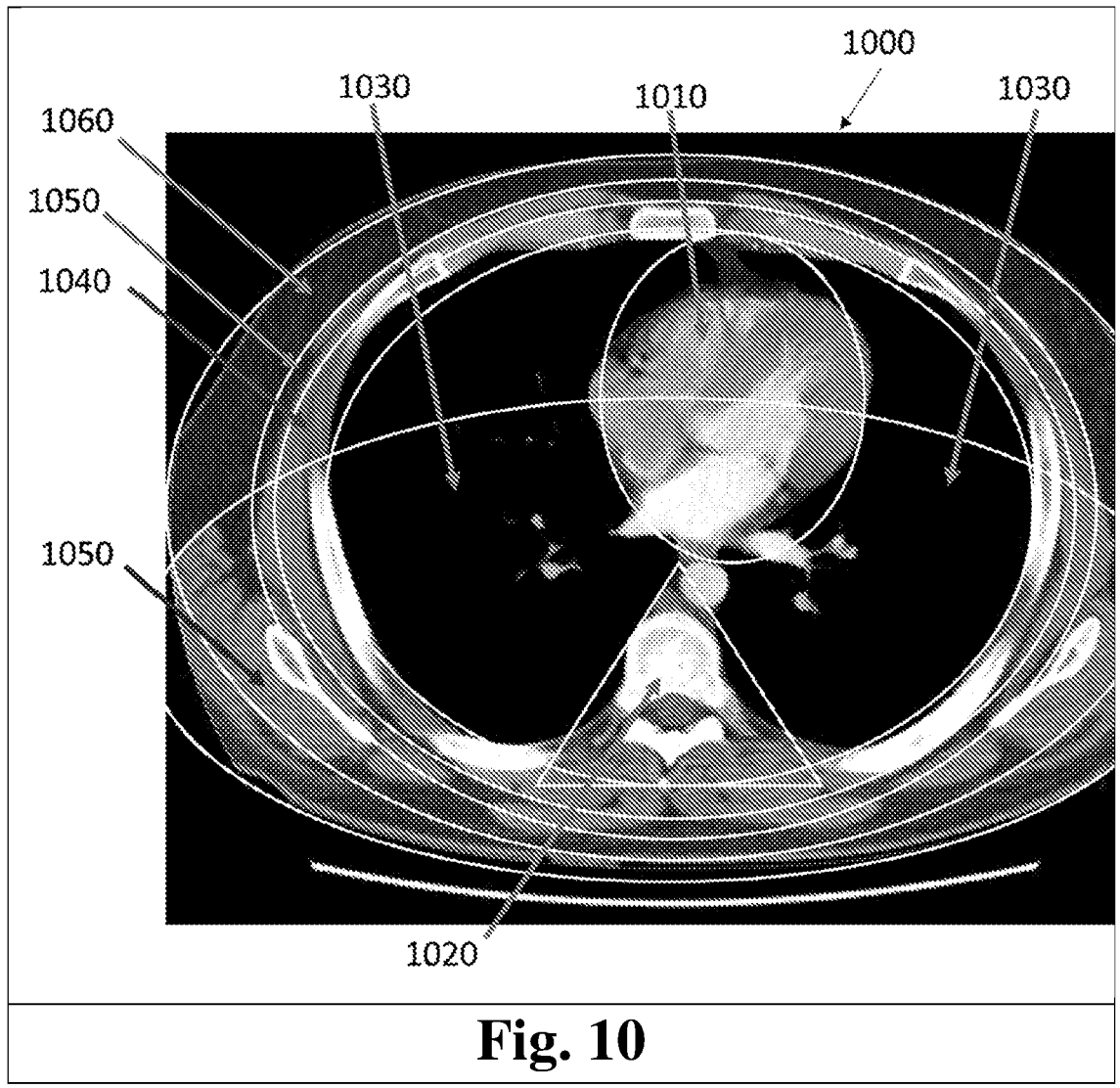
FIG. 10 illustrates a CT image of a horizontal slice through a normal human chest at the level of the heart, with overlay lines to show the edges of a simplified geometry for a simulation.

A simulation of a method of generating a thermal diffusion image is demonstrated on a horizontal slice of a human thorax (chest), which includes the lungs and the heart. FIG. 10 shows a CT image of a normal human thorax (1000), showing the heart (1010), spine (1020), lungs (1030), and the bones (1040), muscles (1050) and fat (1060). These have been overlaid with lines indicating the simplified shapes for the organs which will be used in the simulation. The spine (1020) is simulated by a triangle, the heart (1010) by an oval, with the inner and outer limits of the bone (1040), muscle (1050) and fat (1060) being indicated by concentric ovals. The lungs (1030) occupy the space between the oval of the heart (1010) and the triangle of the spine (1020) as inner limits to the lungs and the inner perimeter of the bone (1040) as the outer limits to the bone.

Figure 11:
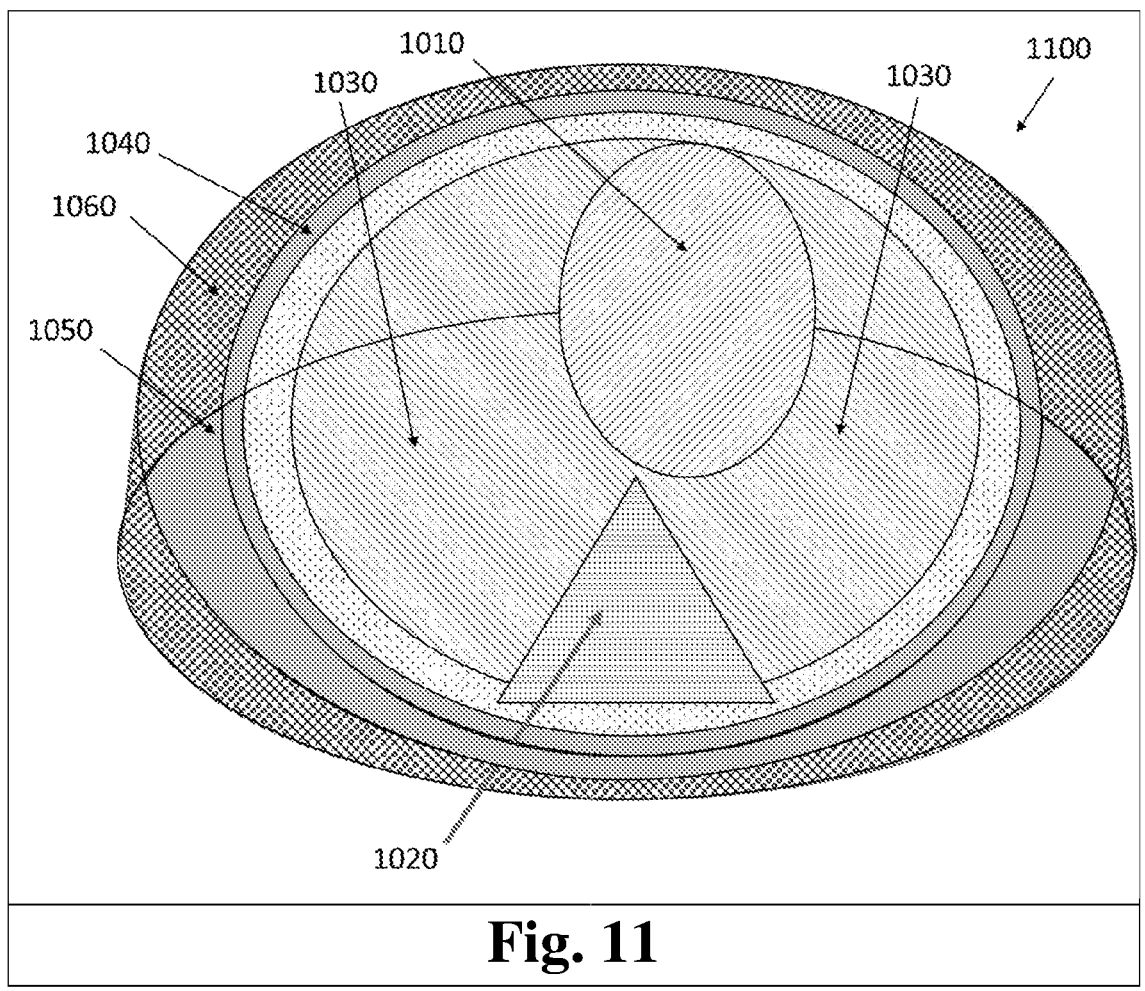
FIG. 11 illustrates the simplified geometry used for simulation, including a simplified heart, simplified skin, muscle and bone, and an exemplary growth.

FIG. 11 shows the simplified shapes of the organs (1100), without the CT scan. In FIG. 11, the heart (1010) is indicated by the oval filled with right diagonal lines, the spine (1020) by the triangle with horizontal lines, the lungs (1030) by left diagonal lines, the bones (1040) by the dotted region outside the lungs, the muscles (1050) by the grey region, and the fat (1060) by the outermost, diamond-filled region. The width of the slice, side-to-side, is approximately 30 cm.

Table 1 shows the physical parameters used in the simulation.

TABLE 1

Physical parameters used in the simulation

| Tissue Type | Density $(kg/m^3)$ | Thermal Conductivity k $(W/(m\ K))$ | Specific Heat $c_p$ $(J/(kg\ K))$ | Perfussion $(ml/(min\ gm))$ | Heat Generation Rate Q $(W/m^3)$ |
|---|---|---|---|---|---|
| Air | 1.205 | 0.0257 | 1005 | — | 0 |
| Lung | 427 | 0.38 | 3886 | 0.04 | 600 |
| Cortical Bone | 1460 | 0.295 | 1244 | 0.027 | 0 |
| Cancellous Bone | 1460 | 0.295 | 2292 | 0.027 | 0 |
| Muscle | 1103 | 0.49 | 3322 | 0.0009 | 684 |
| Fat | 909 | 0.21 | 2065 | 0.0002 | 58 |
| Blood | 1060 | 0.51 | 3651 | — | 0 |
| Heart | 1086 | 0.55 | 3669 | 1.17 | 700 |
| Tumor | 1050 | 0.561 | 3852 | 0.009 | 5000 |

Figure 12:
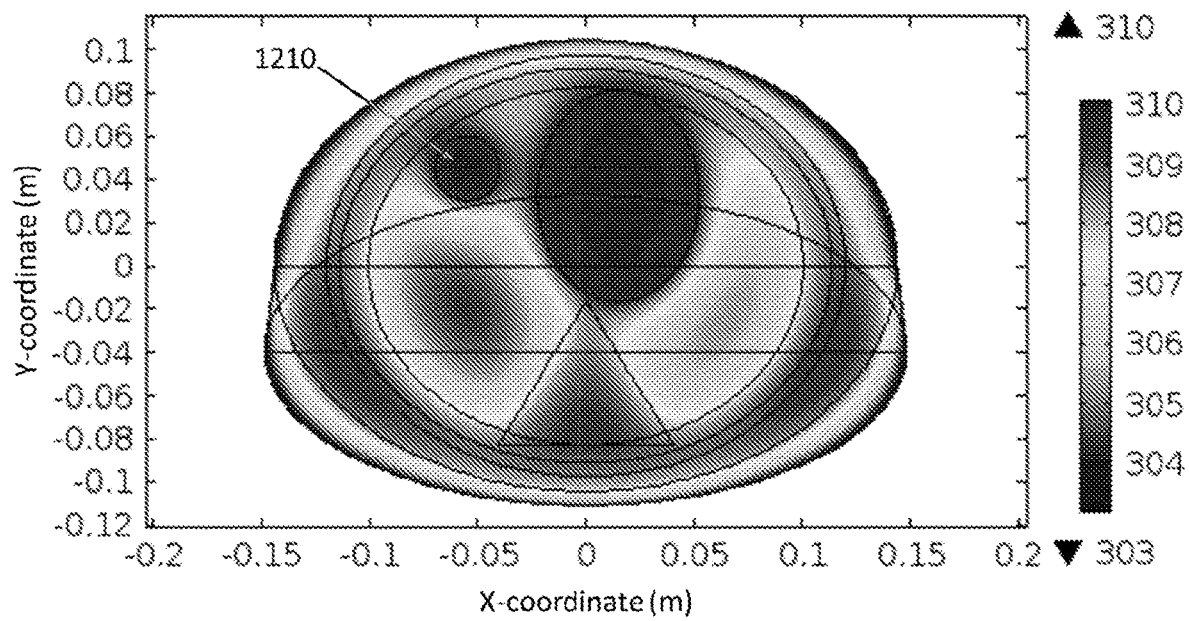
FIG. 12 illustrates a simulation of a steady-state temperature map of the slice of the chest.

FIG. 12 illustrates a simulated steady-state heat distribution in a chest with a growth (1210) in the lungs. The center of the growth is at an x-coordinate of about −0.055 m. The initial conditions for the simulation were a uniform temperature of 37° C. (310 K), with a heat transfer coefficient at the skin boundary of about 10 and radiative heat transfer from the skin. Of the normal tissue, the heart is the hottest part of the simulation, at approximately 310 K, while the lungs, at approximately 304-306 K, are the coolest, while the bone and muscle are about 308-309 K. The skin is at about 303 K, with the temperature in the fat rising form about 303 K to about 306 K. The growth (1210), at about 310 K, is clearly seen on the left side of the figure.

Figure 13:
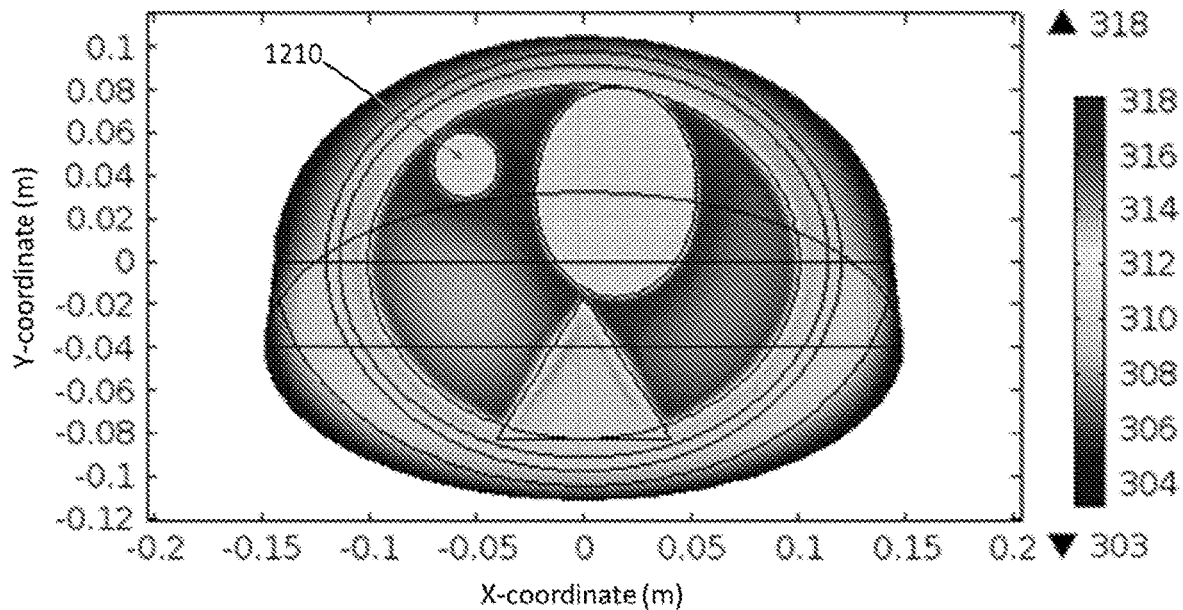
FIG. 13 illustrates a simulation of a temperature map of the slice of the chest after inhalation of a hot gas.

FIG. 13 illustrates the effect of inhaling a hot gas on the temperature distribution inside the chest. In this simulation, the gas was at a temperature of 50° C. (323 K) and was "inhaled" (provided to the lungs as a heat generation source) for 30 s.

Figure 14:
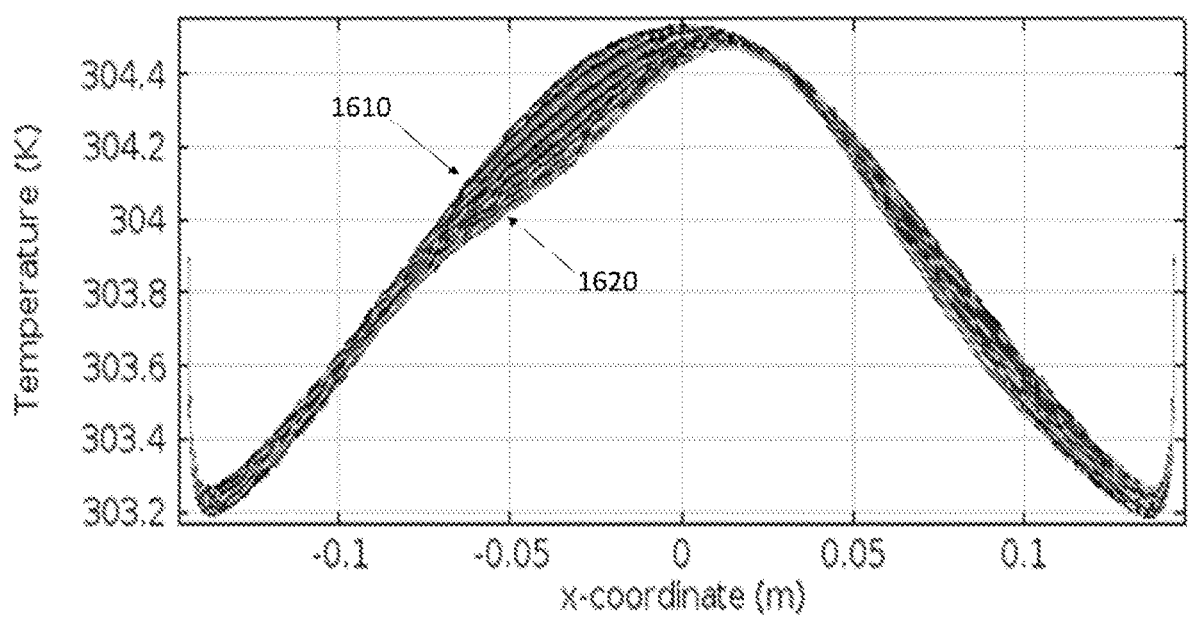
FIG. 14 illustrates a simulation of the change in the temperature profile as the chest cools back to its steady state temperature profile after heating.

FIG. 14 illustrates the change in the temperature profile as measured outside the chest, for example by an imaging device such as an IR camera, as the chest cools back to its steady state temperature profile after heating. The uppermost curve (1610) illustrates the temperature profile immediately after completion of inhalation of the hot gas, while the lowermost curve (1620) illustrates the steady-state temperature profile. The anomaly (the growth 1210) is clearly present, although its center appears to be at about −0.03, rather than the known central position of about −0.55.

These simulations show that the presence and approximate location of an anomaly can be determined from outside the chest, that heating from inside the lungs materially affects the temperature profile inside the body, and that this change in internal temperature profile is determinable from outside the body.

While the invention is susceptible to various modifications and alternative forms, specific embodiments thereof have been shown by way of example in the drawings and the above detailed description. It should be understood, however, that it is not intended to limit the invention to the particular forms disclosed, but on the contrary, the intention is to cover all modifications, equivalents, and alternatives falling within the spirit and scope of the invention as defined by the appended claims.

The invention claimed is:

1. A method of detecting and diagnosing of at least one irregularity in an examined tissue, characterized by steps of:
actively thermomodulating at least a portion of said examined tissue, said active thermomodulation selected from a group consisting of heating, cooling and any combination thereof, said active thermomodulation applied according to a pre-determined protocol selected from a group consisting of: in a continuous manner, in a pulsed manner and any combination thereof;
collecting time-resolved thermal data at predetermined time intervals over time t, for a plurality of coordinated locations of at least a portion of said examined tissue;
calculating according to said time-resolved thermal data, (a) a thermal transfer index, I, for each of said plurality of coordinated locations; and (b) a ratio between each said thermal transfer index for each of said plurality of coordinated locations; and
wherein at least one of the following steps is being held true:
determining tissue at least one of said plurality of coordinated locations as irregular if, for said at least one of said plurality of coordinated locations, said I is greater than a measured value I of a baseline tissue; and
determining tissue at a first coordinated location as irregular if, for at least two of said plurality of coordinated locations, a ratio between a first $I_{first}$ for a first coordinated location and a second $I_{second}$ for a second coordinated location is greater than a predetermined value $I_{tir}$, further wherein said processor is configured to generate a visual presentation of said coordinated locations according to said I or an inferential thereof, further comprising a step of defining said I according to the following formula:

$$T=a+b*\exp(-I*t)$$

where T is temperature at said time t and a and b are constants.

2. The method according to claim 1, further comprising at least one of the following steps:

selecting said at least one irregularity from a group consisting of a malignant tumor, a precancerous tumor, a benign tumor, neoplasm, an infection, pneumonia, a necrotic cell, a blood clot and any combination thereof;

selecting said examined tissue from a group consisting of lung tissue, skin, cervical tissue, ear tissue, nose tissue, throat tissue, oral tissue, esophageal tissue, stomach tissue, intestinal tissue, colon tissue, rectal tissue, kidney tissue, uterine tissue, urinary tract tissue, bladder tissue, prostate tissue, eye tissue, and any combination thereof; and selecting said time t to be in a range from about 10 ns to about 10 min.

3. The method according to claim 1, further comprising steps of collecting said thermal data using at least one sensor and of selecting said at least one sensor from a group consisting of: an IR sensor, Ultrasound a mercury-in-glass thermometer, pill thermometer, liquid crystal thermometer, thermocouple, thermistor, resistance temperature detector, silicon bandgap temperature sensor and any combination thereof.

4. The method according to claim 1, further comprising at least one of the following steps:

producing at least one heat diffusion image of at least a portion of said examined tissue prior to said active thermomodulation;

image processing said at least one heat diffusion image by at least one object recognition module, thereby identifying coordinated locations suspected of containing at least one said irregularity; and providing at least one spatial positioner selected from a group consisting of a visible light imaging means, a CCD camera, an ultrasound scanner, a thermal camera, a laser rangefinder and any combination thereof, and correlating said at least one heat diffusion image and at least one image from said at least one spatial positioner.

5. The method according to claim 1, further comprising a providing a normalization step, at least one of the following being held true:

said normalizing step comprises normalizing said I to a predetermined scale, a higher value on said scale indicating a higher severity of the medical condition of said at least one irregularity;

said normalizing step is selected from a group consisting of correcting for ambient temperature, correcting for ambient humidity, correcting for ambient electromagnetic radiation and any combination thereof; and said heat transfer index is normalized with patient parameters selected from a group consisting of sex, age, smoking habits, drinking habits, number of births, height, weight, blood pressure, diabetes state, medical history, relatives medical history, patients previous heat transfer index and any combination thereof.

6. The method according to claim 1, further comprising steps of selecting said active thermomodulation from a group consisting of advecting heat, convecting heat, conducting heat, irradiating and any combination thereof; and of selecting said active thermomodulation device from a group consisting of hot fluid inhalation, cold fluid inhalation, hot fluid application, cold fluid application, halogen lamp exposure, LED light exposure, xenon lamp exposure, flash lamp exposure, incandescent lamp exposure, IR emission, electromagnetic vibration heating, mechanical vibration heating, positioning a heatable solid, positioning a coolable solid, positioning a heatable patch, positioning a coolable patch, pharmaceutical temperature modification, chemically induced heating, chemically induced cooling and any combination thereof.

7. A system for detecting, diagnosing and guiding treatment of at least one irregularity in an examined tissue, comprising:

an active thermomodulator configured to apply to at least a portion of said examined tissue a member of a group consisting of: heating cooling and any combination thereof, said active thermomodulation applicable according to a pre-determined protocol selected from a group consisting of: in a continuous manner, in a pulsed manner and any combination thereof;

at least one thermal sensor configured to provide at least one signal related to temperature in at least a part of said at least a portion of said examined tissue; and a processor configured to execute instructions comprising:

collect time-resolved thermal data, at predetermined intervals over time t, of a plurality of coordinated locations of at least a portion of said examined tissue by conversion of said signal from said at least one thermal sensor to time-resolved and spatially-resolved thermal data; and calculate, according to said time-resolved thermal data, (a) a thermal transfer index, I, for each of said plurality of coordinated locations; and (b) a ratio between each said thermal transfer index for each of said plurality of coordinated locations; and wherein at least one of the following is being held true:

if, for at least one of said plurality of coordinated locations, said I is greater than a measured value I of a baseline tissue, determining tissue at said least one coordinated location as irregular; and if, for at least two of said plurality of coordinated locations, a ratio between a first $I_{first}$ of a first coordinated location and a second $I_{second}$ of a second coordinated location is greater than a predetermined value $I_{irr}$, determining tissue at said first coordinated location as irregular;

further wherein said processor is configured to generate a three-dimensional thermal map of said at least a portion of said examined tissue, wherein said I is defined according to the following formula:

$$T=a+b*\exp(-I*t)$$

where T is temperature at said time t and a and b are constants.

8. The system according to claim 7, wherein at least one of the following is held true:

said at least one irregularity is selected from a group consisting of a malignant tumor, a precancerous tumor, a benign tumor, neoplasm, an infection, pneumonia, a necrotic cell, a blood clot and any combination thereof;

said examined tissue is selected from a group consisting of lung tissue, skin, cervical tissue, ear tissue, nose tissue, throat tissue, oral tissue, esophageal tissue, stomach tissue, intestinal tissue, colon tissue, rectal tissue, kidney tissue, uterine tissue, urinary tract tissue, bladder tissue, prostate tissue, eye tissue, and any combination thereof; and said time t is selected to be in a range from about 10 ns to about 10 min.

9. The system according to claim 7, wherein said at least one sensor is selected from a group consisting of: an IR sensor, ultrasound a mercury-in-glass thermometer, pill thermometer, liquid crystal thermometer, thermocouple, thermistor, resistance temperature detector, silicon bandgap temperature sensor and any combination thereof.

10. The system according to claim 7, wherein at least one of the following is held true:
at least one heat diffusion image of at least a portion of said examined tissue is producible prior to said active thermomodulation;
at least one coordinated location suspected of containing at least one irregularity is identifiable by means of image processing of said at least one heat diffusion image by at least one object recognition module; and
said system additionally comprises at least one spatial positioner selected from a group consisting of: a visible light imaging means, a CCD camera, a skin dermoscope, a microscope, an ultrasound scanner, a thermal camera, a laser rangefinder and any combination thereof, and said processor additionally comprises instructions configured to correlate said at least one heat diffusion image and at least one image from said at least one spatial positioner.

11. The system according to claim 7, wherein said computer processor additionally comprises instructions to provide a normalization step, at least one of the following being held true:
said normalizing step comprises normalizing said I to a predetermined scale, a higher value on said scale indicating a higher severity of the medical condition of said at least one irregularity;
said normalizing step is selected from a group consisting of correcting for ambient temperature, correcting for ambient humidity, correcting for ambient electromagnetic radiation and any combination thereof; and
said heat transfer index is normalized with patient parameters selected from a group consisting of sex, age, smoking habits, drinking habits, number of births, height, weight, blood pressure, diabetes state, medical history, relatives medical history, patients previous heat transfer index and any combination thereof.

12. The system according to claim 7, wherein said active thermomodulation is selected from a group consisting of advecting heat, convecting heat, conducting heat, irradiating and any combination thereof; and said active thermomodulation device is selected from a group consisting of hot fluid inhalation, cold fluid inhalation, hot fluid application, cold fluid application, halogen lamp exposure, LED light exposure, xenon lamp exposure, flash lamp exposure, incandescent lamp exposure, IR emission, electromagnetic vibration heating, mechanical vibration heating, positioning a heatable solid, positioning a coolable solid, positioning a heatable patch, positioning a coolable patch, pharmaceutical temperature modification, chemically induced heating, chemically induced cooling and any combination thereof.

13. A non-transitory computer readable medium (CRM) having instructions which, when implemented by one or more computers, causes said one or more computers to:
collect time-resolved thermal data, at predetermined intervals over time t, of a plurality of coordinated locations of at least a portion of said examined tissue by conversion of said signal from said at least one thermal sensor to time-resolved and spatially-resolved thermal data; and
calculate, according to said time-resolved thermal data, (a) a thermal transfer index, I, for each of said plurality of coordinated locations; and (b) a ratio between each said thermal transfer index for each of said plurality of coordinated locations; and
wherein at least one of the following is being held true:
if, for at least one of said plurality of coordinated locations, said I is greater than a measured value I of a baseline tissue, determining tissue at said least one coordinated location as irregular; and
if, for at least two of said plurality of coordinated locations, a ratio between a first $I_{first}$ of a first coordinated location and a second $I_{second}$ of a second coordinated location is greater than a predetermined value $I_{irr}$, determining tissue at said first coordinated location as irregular, wherein said I is defined
according to the following formula:

$$T=a+b*\exp(-I*t)$$

where T is temperature at said time t and a and b are constants.

14. The CRM according to claim 13, wherein at least one of the following is held true:
said at least one irregularity is selected from a group consisting of a malignant tumor, a precancerous tumor, a benign tumor, neoplasm, an infection, pneumonia, a necrotic cell, a blood clot and any combination thereof;
said examined tissue is selected from a group consisting of lung tissue, skin, cervical tissue, ear tissue, nose tissue, throat tissue, oral tissue, esophageal tissue, stomach tissue, intestinal tissue, colon tissue, rectal tissue, kidney tissue, uterine tissue, urinary tract tissue, bladder tissue, prostate tissue, eye tissue, and any combination thereof; and
said time t is selected to be in a range from about 10 ns to about 10 min.

15. The CRM according to claim 13, additionally comprising instructions configured to execute at least one of the following:
produce at least one heat diffusion image of at least a portion of said examined tissue prior to said active thermomodulation;
identify at least one coordinated location suspected of containing at least one irregularity by means of image processing of said at least one heat diffusion image by at least one object recognition module; and
correlate said at least one heat diffusion image and at least one image from at least one spatial positioner, said at least one spatial positioner selected from a group consisting of: a visible light imaging means, a CCD camera, an ultrasound scanner, a thermal camera, a laser rangefinder and any combination thereof.

16. The CRM according to claim 13, additionally comprising instructions configured to provide a normalization step, at least one of the following being held true:
said normalizing step comprises normalizing said I to a predetermined scale, a higher value on said scale indicating a higher severity of the medical condition associated with said at least one irregularity;

said normalizing step is selected from a group consisting of correcting to ambient temperature, correcting to ambient humidity, correcting to ambient electromagnetic radiation and any combination thereof; and said heat transfer index is normalized with patient parameters selected from a group consisting of sex, age, smoking habits, drinking habits, number of births, height, weight, blood pressure, diabetes state, medical history, relatives medical history, patients previous heat transfer index and any combination thereof.

17. The CRM according to claim 13, wherein said active thermomodulation is selected from a group consisting of advecting heat, convecting heat, conducting heat, irradiating and any combination thereof; and said active thermomodulation device is selected from a group consisting of hot fluid inhalation, cold fluid inhalation, hot fluid application, cold fluid application, halogen lamp exposure, LED light exposure, xenon lamp exposure, flash lamp exposure, incandescent lamp exposure, IR emission, electromagnetic vibration heating, mechanical vibration heating, positioning a heatable solid, positioning a coolable solid, positioning a heatable patch, positioning a coolable patch, pharmaceutical temperature modification, chemically induced heating, chemically induced cooling and any combination thereof.

\* \* \* \* \*